(12) United States Patent
Stone et al.

(10) Patent No.: US 7,914,539 B2
(45) Date of Patent: Mar. 29, 2011

(54) TISSUE FIXATION DEVICE

(75) Inventors: Kevin T Stone, Winona Lake, IN (US); H. Gene Hawkins, Warsaw, IN (US); Zachary M Hoffman, Minneapolis, MN (US); Gregory J Denham, Warsaw, IN (US); Troy M Walters, Plymouth, IN (US); Ryan A Kaiser, Leesburg, IN (US); Jason D Meridew, Syracuse, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1513 days.

(21) Appl. No.: 11/294,694

(22) Filed: Dec. 5, 2005

(65) Prior Publication Data

US 2006/0100627 A1  May 11, 2006

Related U.S. Application Data

(63) Continuation-in-part of application No. 10/984,624, filed on Nov. 9, 2004, now Pat. No. 7,608,098.

(51) Int. Cl.
*A61B 17/58* (2006.01)
*A61B 17/04* (2006.01)
*A61B 17/86* (2006.01)

(52) U.S. Cl. ............... 606/104; 606/76; 606/77; 606/99; 606/304; 606/319; 623/13.14

(58) Field of Classification Search ............... 606/77, 606/99, 104, 302, 304, 314, 315, 907, 908, 606/909, 913, 76; 623/13.14, 23.44, 919
See application file for complete search history.

(56) References Cited

U.S. PATENT DOCUMENTS

| | | | |
|---|---|---|---|
| 26,501 | A | 10/1859 | Kendrick et al. |
| 126,366 | A | 4/1872 | Willis |
| 233,475 | A | 10/1880 | Cook et al. |
| 261,501 | A | 7/1882 | Vandermark |
| 417,805 | A | 12/1889 | Beaman |
| 487,304 | A | 12/1892 | Todd |
| 837,767 | A | 12/1906 | Aims |
| 1,059,631 | A | 4/1913 | Popovics |
| 1,131,155 | A | 3/1915 | Murphy |

(Continued)

FOREIGN PATENT DOCUMENTS

AU  49572/64  3/1966

(Continued)

OTHER PUBLICATIONS

Arthrotek, A Biomet Company; Knees; Sure fire Hybrid Meniscal Device.

(Continued)

*Primary Examiner* — Thomas C Barrett
*Assistant Examiner* — Christian Sevilla
(74) *Attorney, Agent, or Firm* — Harness, Dickey

(57) ABSTRACT

A fixation device for securing tissue to a bone. The fixation device includes an anchor having a hollow body defining a longitudinal passage, and a plug configured to be received in at least a portion of the passage. The body comprises a cylindrical portion and a tapered tip portion. The cylindrical portion comprises a plurality of thin-walled window covers such that after implantation the window covers are resorbed first relative to other portions of the cylindrical portion for defining a plurality of apertures on the cylindrical portion.

13 Claims, 17 Drawing Sheets

U.S. PATENT DOCUMENTS

| | | |
|---|---|---|
| 1,153,450 A | 9/1915 | Schaff |
| 1,635,066 A | 7/1927 | Wells |
| 401,677 A | 11/1933 | Roeder |
| 2,065,659 A | 12/1936 | Cullen |
| 2,108,206 A | 2/1938 | Meeker |
| 2,242,003 A | 5/1941 | Lorenzo |
| 2,302,986 A | 11/1942 | Vollrath |
| 2,397,216 A * | 3/1946 | Stellin .......................... 411/404 |
| RE22,857 E | 3/1947 | Ogburn |
| 2,526,959 A | 10/1950 | Lorenzo |
| 2,562,419 A | 7/1951 | Ferris |
| 2,581,564 A | 1/1952 | Villegas |
| 2,610,631 A | 9/1952 | Calicchio |
| 2,669,774 A | 2/1954 | Mitchell |
| 2,760,488 A | 8/1956 | Pierce |
| 2,833,284 A | 5/1958 | Springer |
| 2,846,712 A | 8/1958 | Markman |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,013,559 A | 12/1961 | Thomas |
| 3,037,619 A | 6/1962 | Stevans |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,240,379 A | 3/1966 | Bremer et al. |
| 3,399,432 A | 9/1968 | Merser |
| RE26,501 E | 12/1968 | Kendrick et al. |
| 3,470,834 A | 10/1969 | Bone |
| 3,470,875 A | 10/1969 | Johnson |
| 3,500,820 A | 3/1970 | Almen |
| 3,515,132 A | 6/1970 | McKnight |
| 3,527,223 A | 9/1970 | Shein |
| 3,541,591 A | 11/1970 | Hoegerman |
| 3,547,389 A | 12/1970 | Mitchell |
| 3,579,831 A | 5/1971 | Stevens |
| 3,618,447 A | 11/1971 | Goins |
| 3,643,649 A | 2/1972 | Amato |
| 3,664,345 A | 5/1972 | Dabbs et al. |
| 3,675,639 A | 7/1972 | Cimber |
| 3,695,271 A | 10/1972 | Chodorow |
| 3,699,969 A | 10/1972 | Allen |
| 3,716,058 A | 2/1973 | Tanner, Jr. |
| 3,752,516 A | 8/1973 | Mumma |
| 3,757,629 A | 9/1973 | Schneider |
| 3,807,407 A | 4/1974 | Schweizer |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,907,442 A | 9/1975 | Reid |
| 3,910,281 A | 10/1975 | Kletschka et al. |
| 3,931,667 A | 1/1976 | Merser et al. |
| 3,943,932 A | 3/1976 | Woo |
| 3,946,740 A | 3/1976 | Bassett |
| 3,954,103 A | 5/1976 | Garcia-Roel et al. |
| 3,961,632 A | 6/1976 | Moossun |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,006,747 A | 2/1977 | Kronenthal et al. |
| 4,007,743 A | 2/1977 | Blake |
| 4,013,071 A | 3/1977 | Rosenberg |
| 4,084,478 A * | 4/1978 | Simmons ........................ 411/404 |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,144,876 A | 3/1979 | DeLeo |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,275,717 A | 6/1981 | Bolesky |
| 4,287,807 A | 9/1981 | Pacharis et al. |
| 4,291,698 A | 9/1981 | Fuchs et al. |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | DiFrancesco |
| 4,402,445 A | 9/1983 | Green |
| 4,409,974 A | 10/1983 | Freedland |
| 4,438,769 A | 3/1984 | Pratt et al. |
| 4,454,875 A | 6/1984 | Pratt et al. |
| 4,462,395 A | 7/1984 | Johnson |
| 4,463,753 A | 8/1984 | Gustilo |
| 4,484,570 A | 11/1984 | Sutter et al. |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,537,185 A | 8/1985 | Stednitz |
| 4,561,432 A | 12/1985 | Mazor |
| 4,570,623 A | 2/1986 | Ellison et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,653,487 A | 3/1987 | Maale |
| 4,653,489 A | 3/1987 | Tronzo |
| 4,662,068 A | 5/1987 | Polonsky |
| 4,667,675 A | 5/1987 | Davis |
| 4,669,473 A | 6/1987 | Richards et al. |
| 4,683,895 A | 8/1987 | Pohndorf |
| 4,705,040 A | 11/1987 | Mueller et al. |
| 4,716,893 A | 1/1988 | Fischer et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,738,255 A | 4/1988 | Goble et al. |
| 4,741,330 A | 5/1988 | Hayhurst |
| 4,741,336 A | 5/1988 | Failla et al. |
| 4,750,492 A | 6/1988 | Jacobs |
| 4,760,843 A | 8/1988 | Fischer et al. |
| 4,772,261 A | 9/1988 | Von Hoff et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Clarén |
| 4,790,297 A | 12/1988 | Luque |
| 4,809,695 A | 3/1989 | Gwathmey et al. |
| 4,823,794 A | 4/1989 | Pierce |
| 4,832,026 A | 5/1989 | Jones |
| 4,834,098 A | 5/1989 | Jones |
| 4,841,960 A | 6/1989 | Garner |
| 4,858,608 A | 8/1989 | McQuilkin |
| 4,860,513 A | 8/1989 | Whitman |
| 4,870,957 A | 10/1989 | Goble et al. |

| Patent No. | Date | Name |
|---|---|---|
| 4,873,976 A | 10/1989 | Schreiber |
| 4,887,601 A | 12/1989 | Richards |
| 4,890,615 A | 1/1990 | Caspari et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,901,721 A | 2/1990 | Hakki |
| 4,923,461 A | 5/1990 | Caspari et al. |
| 4,927,421 A | 5/1990 | Goble et al. |
| 4,946,468 A | 8/1990 | Li |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Törmälä et al. |
| 4,976,736 A | 12/1990 | White et al. |
| 4,978,350 A | 12/1990 | Wagenknecht |
| 4,983,176 A | 1/1991 | Cushman et al. |
| 5,002,562 A | 3/1991 | Oberlander |
| 5,041,129 A | 8/1991 | Hayhurst et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,098,435 A | 3/1992 | Stednitz et al. |
| 5,123,913 A | 6/1992 | Wilk et al. |
| 5,129,901 A | 7/1992 | Decoste |
| 5,129,904 A | 7/1992 | Illi |
| 5,139,499 A | 8/1992 | Small et al. |
| 5,143,498 A | 9/1992 | Whitman |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,169,400 A | 12/1992 | Mühling et al. |
| 5,176,682 A | 1/1993 | Chow |
| 5,178,629 A | 1/1993 | Kammerer |
| 5,192,282 A | 3/1993 | Draenert |
| 5,203,784 A | 4/1993 | Ross et al. |
| 5,203,787 A | 4/1993 | Noblitt et al. |
| 5,209,805 A | 5/1993 | Spraggins |
| 5,211,647 A | 5/1993 | Schmieding |
| 5,211,650 A | 5/1993 | Noda |
| 5,214,987 A * | 6/1993 | Fenton, Sr. ................ 81/460 |
| 5,242,447 A | 9/1993 | Borzone |
| 5,249,899 A | 10/1993 | Wilson |
| 5,258,015 A | 11/1993 | Li et al. |
| 5,269,160 A | 12/1993 | Wood |
| 5,269,783 A | 12/1993 | Sander |
| 5,269,809 A | 12/1993 | Hayhurst et al. |
| 5,282,809 A | 2/1994 | Kammerer et al. |
| 5,312,438 A | 5/1994 | Johnson |
| 5,318,577 A | 6/1994 | Li |
| 5,318,578 A | 6/1994 | Hasson |
| 5,320,633 A | 6/1994 | Allen et al. |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,342,369 A | 8/1994 | Harryman, II |
| 5,354,292 A * | 10/1994 | Braeuer et al. ................ 606/1 |
| 5,354,299 A * | 10/1994 | Coleman ................ 606/916 |
| 5,358,511 A | 10/1994 | Gatturna et al. |
| 5,360,431 A | 11/1994 | Puno et al. |
| 5,364,400 A | 11/1994 | Rego, Jr. et al. |
| 5,374,268 A | 12/1994 | Sander |
| 5,383,878 A | 1/1995 | Roger et al. |
| 5,391,171 A | 2/1995 | Schmieding |
| RE34,871 E | 3/1995 | McGuire et al. |
| 5,397,356 A | 3/1995 | Goble et al. |
| 5,403,348 A | 4/1995 | Bonutti |
| 5,417,691 A | 5/1995 | Hayhurst |
| 5,423,819 A | 6/1995 | Small et al. |
| 5,425,766 A | 6/1995 | Bowald |
| 5,433,751 A | 7/1995 | Christel et al. |
| 5,437,680 A | 8/1995 | Yoon |
| 5,439,684 A | 8/1995 | Prewett et al. |
| 5,443,509 A | 8/1995 | Boucher et al. |
| 5,447,512 A | 9/1995 | Wilson et al. |
| 5,456,685 A | 10/1995 | Huebner |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,474,572 A | 12/1995 | Hayhurst |
| 5,484,442 A | 1/1996 | Melker et al. |
| 5,490,750 A | 2/1996 | Gundy |
| 5,496,331 A | 3/1996 | Xu et al. |
| 5,505,736 A | 4/1996 | Reimels et al. |
| 5,520,691 A | 5/1996 | Branch |
| 5,522,820 A | 6/1996 | Caspari et al. |
| 5,522,846 A | 6/1996 | Bonutti |
| 5,527,342 A | 6/1996 | Pietrzak et al. |
| 5,527,343 A | 6/1996 | Bonutti |
| 5,545,178 A | 8/1996 | Kensey et al. |
| 5,545,228 A | 8/1996 | Kambin |
| 5,549,630 A | 8/1996 | Bonutti |
| 5,549,631 A | 8/1996 | Bonutti |
| 5,571,139 A | 11/1996 | Jenkins, Jr. |
| 5,573,286 A | 11/1996 | Rogozinski |
| 5,573,548 A | 11/1996 | Nazre et al. |
| 5,584,862 A | 12/1996 | Bonutti |
| 5,591,207 A | 1/1997 | Coleman |
| 5,593,407 A | 1/1997 | Reis |
| 5,601,557 A | 2/1997 | Hayhurst |
| 5,601,559 A | 2/1997 | Melker et al. |
| 5,601,571 A | 2/1997 | Moss |
| 5,632,745 A * | 5/1997 | Schwartz ................ 606/75 |
| 5,641,256 A | 6/1997 | Gundy |
| 5,643,269 A | 7/1997 | Härle |
| 5,643,320 A | 7/1997 | Lower et al. |
| 5,645,546 A | 7/1997 | Fard |
| 5,645,547 A | 7/1997 | Coleman |
| 5,647,874 A | 7/1997 | Hayhurst |
| 5,658,289 A | 8/1997 | Boucher et al. |
| 5,658,299 A | 8/1997 | Hart |
| 5,658,313 A | 8/1997 | Thal |
| 5,665,112 A | 9/1997 | Thal |
| 5,679,723 A | 10/1997 | Cooper et al. |
| 5,683,419 A | 11/1997 | Thal |
| 5,688,285 A | 11/1997 | Yamada |
| 5,690,678 A | 11/1997 | Johnson |
| 5,695,497 A | 12/1997 | Stahelin |
| 5,697,929 A | 12/1997 | Mellinger |
| 5,702,397 A | 12/1997 | Goble et al. |
| 5,702,462 A | 12/1997 | Oberlander |
| 5,707,373 A | 1/1998 | Sevrain et al. |
| 5,713,904 A | 2/1998 | Errico et al. |
| 5,716,359 A | 2/1998 | Ojima et al. |
| 5,718,717 A | 2/1998 | Bonutti |
| 5,720,765 A | 2/1998 | Thal |
| 5,725,549 A | 3/1998 | Lam |
| 5,725,556 A | 3/1998 | Moser et al. |
| 5,725,581 A | 3/1998 | Brånemark |
| 5,728,109 A | 3/1998 | Schulze et al. |
| 5,728,136 A | 3/1998 | Thal |
| 5,733,306 A | 3/1998 | Bonutti |
| 5,743,912 A | 4/1998 | Lahille et al. |
| 5,746,754 A | 5/1998 | Chan |
| 5,749,898 A | 5/1998 | Schulze et al. |
| 5,766,176 A | 6/1998 | Duncan |
| 5,769,899 A | 6/1998 | Schwartz et al. |
| 5,776,196 A | 7/1998 | Matsuzaki et al. |
| 5,782,864 A | 7/1998 | Lizardi |
| 5,792,142 A | 8/1998 | Galitzer |
| 5,796,127 A | 8/1998 | Hayafuji et al. |
| 5,797,928 A | 8/1998 | Kogasaka |
| 5,800,407 A | 9/1998 | Eldor |
| 5,810,848 A | 9/1998 | Hayhurst |
| 5,814,069 A | 9/1998 | Schulze et al. |
| 5,814,070 A | 9/1998 | Borzone et al. |
| 5,843,084 A | 12/1998 | Hart et al. |

| | | | | | | |
|---|---|---|---|---|---|---|
| 5,846,254 | A | 12/1998 | Schulze et al. | 6,379,361 | B1 | 4/2002 | Beck, Jr. et al. |
| 5,860,973 | A | 1/1999 | Michelson | 6,383,199 | B1 | 5/2002 | Carter et al. |
| 5,868,740 | A | 2/1999 | LeVeen et al. | 6,387,113 | B1 | 5/2002 | Hawkins et al. |
| 5,871,484 | A | 2/1999 | Spievack et al. | 6,387,129 | B2 | 5/2002 | Rieser et al. |
| 5,871,486 | A | 2/1999 | Huebner et al. | 6,398,785 | B2 | 6/2002 | Carchidi et al. |
| 5,871,490 | A | 2/1999 | Schulze et al. | 6,409,743 | B1 | 6/2002 | Fenton, Jr. |
| 5,891,168 | A | 4/1999 | Thal | 6,413,260 | B1 | 7/2002 | Berrevoets et al. |
| 5,893,592 | A | 4/1999 | Schulze et al. | 6,423,088 | B1 | 7/2002 | Fenton, Jr. |
| 5,895,395 | A | 4/1999 | Yeung | 6,428,562 | B2 | 8/2002 | Bonutti |
| 5,897,564 | A | 4/1999 | Schulze et al. | 6,432,123 | B2 | 8/2002 | Schwartz et al. |
| 5,899,902 | A | 5/1999 | Brown et al. | 6,440,136 | B1 | 8/2002 | Gambale et al. |
| 5,941,439 | A | 8/1999 | Kammerer et al. | 6,454,768 | B1 | 9/2002 | Jackson |
| 5,946,783 | A | 9/1999 | Plociennik et al. | 6,458,134 | B1 | 10/2002 | Songer et al. |
| 5,948,002 | A | 9/1999 | Bonutti | 6,461,373 | B2 | 10/2002 | Wyman et al. |
| 5,951,560 | A | 9/1999 | Simon et al. | 6,464,713 | B2 | 10/2002 | Bonutti |
| 5,954,747 | A | 9/1999 | Clark | 6,468,293 | B2 | 10/2002 | Bonutti et al. |
| 5,961,524 | A | 10/1999 | Crombie | 6,471,707 | B1 | 10/2002 | Miller et al. |
| 5,964,767 | A | 10/1999 | Tapia et al. | 6,475,230 | B1 | 11/2002 | Bonutti et al. |
| 5,964,783 | A | 10/1999 | Grafton et al. | 6,497,901 | B1 | 12/2002 | Royer |
| 5,968,045 | A | 10/1999 | Frazier | 6,500,184 | B1 | 12/2002 | Chan et al. |
| 5,968,047 | A | 10/1999 | Reed | 6,500,195 | B2 | 12/2002 | Bonutti |
| 5,976,127 | A | 11/1999 | Lax | RE37,963 | E | 1/2003 | Thal |
| 5,980,524 | A | 11/1999 | Justin et al. | 6,508,820 | B2 | 1/2003 | Bales |
| 5,980,558 | A | 11/1999 | Wiley | 6,508,821 | B1 | 1/2003 | Schwartz et al. |
| 5,980,559 | A | 11/1999 | Bonutti | 6,511,498 | B1 | 1/2003 | Fumex |
| 5,989,252 | A | 11/1999 | Fumex | 6,517,542 | B1 | 2/2003 | Papay et al. |
| 5,989,256 | A | 11/1999 | Kuslich et al. | 6,517,579 | B1 | 2/2003 | Paulos et al. |
| 5,997,542 | A | 12/1999 | Burke | 6,520,964 | B2 | 2/2003 | Tallarida et al. |
| 5,997,552 | A | 12/1999 | Person et al. | 6,527,777 | B2 | 3/2003 | Justin |
| 6,001,100 | A | 12/1999 | Sherman et al. | 6,527,794 | B1 | 3/2003 | McDevitt et al. |
| 6,010,525 | A | 1/2000 | Bonutti et al. | 6,537,319 | B2 | 3/2003 | Whelan |
| 6,016,727 | A | 1/2000 | Morgan | 6,540,770 | B1 | 4/2003 | Tornier et al. |
| 6,022,352 | A | 2/2000 | Vandewalle | 6,547,564 | B1 | 4/2003 | Hansson |
| 6,022,373 | A | 2/2000 | Li | 6,551,343 | B1 | 4/2003 | Tormala et al. |
| 6,024,758 | A | 2/2000 | Thal | 6,554,830 | B1 | 4/2003 | Chappius |
| 6,039,753 | A | 3/2000 | Meislin | 6,554,852 | B1 | 4/2003 | Oberlander |
| 6,045,574 | A | 4/2000 | Thal | 6,562,071 | B2 | 5/2003 | Järvinen |
| 6,048,343 | A | 4/2000 | Mathis et al. | 6,565,572 | B2 | 5/2003 | Chappius |
| 6,053,916 | A | 4/2000 | Moore | 6,565,573 | B1 | 5/2003 | Ferrante et al. |
| 6,068,648 | A | 5/2000 | Cole et al. | 6,569,187 | B1 | 5/2003 | Bonutti et al. |
| 6,077,292 | A | 6/2000 | Bonutti | 6,572,655 | B1 | 6/2003 | Johnson et al. |
| 6,096,060 | A | 8/2000 | Fitts et al. | 6,585,740 | B2 | 7/2003 | Schlapfer et al. |
| 6,117,160 | A | 9/2000 | Bonutti | 6,589,245 | B1 | 7/2003 | Weiler et al. |
| 6,117,162 | A | 9/2000 | Schmieding et al. | 6,607,548 | B2 | 8/2003 | Pohjonen et al. |
| 6,123,710 | A | 9/2000 | Pinczewski et al. | 6,620,166 | B1 | 9/2003 | Wenstrom, Jr. et al. |
| 6,143,017 | A | 11/2000 | Thal | 6,620,195 | B2 | 9/2003 | Goble et al. |
| 6,149,653 | A | 11/2000 | Deslauriers | 6,623,492 | B1 | 9/2003 | Berube et al. |
| 6,149,669 | A | 11/2000 | Li | 6,623,524 | B2 | 9/2003 | Schmieding |
| 6,156,039 | A | 12/2000 | Thal | 6,629,977 | B1 | 10/2003 | Wolf |
| 6,156,056 | A | 12/2000 | Kearns et al. | 6,635,073 | B2 | 10/2003 | Bonutti |
| 6,159,234 | A | 12/2000 | Bonutti et al. | 6,652,562 | B2 | 11/2003 | Collier et al. |
| 6,190,401 | B1 | 2/2001 | Green et al. | 6,656,182 | B1 | 12/2003 | Hayhurst |
| 6,190,411 | B1 | 2/2001 | Lo | 6,663,634 | B2 | 12/2003 | Ahrens et al. |
| 6,200,330 | B1 | 3/2001 | Benderev et al. | 6,663,656 | B2 | 12/2003 | Schmieding et al. |
| 6,206,883 | B1 | 3/2001 | Tunc | 6,666,868 | B2 | 12/2003 | Fallin |
| 6,210,376 | B1 | 4/2001 | Grayson | 6,689,137 | B2 | 2/2004 | Reed |
| 6,214,012 | B1 | 4/2001 | Karpman et al. | 6,712,849 | B2 | 3/2004 | Re et al. |
| 6,228,096 | B1 | 5/2001 | Marchand | 6,716,957 | B2 | 4/2004 | Tunc |
| 6,231,592 | B1 | 5/2001 | Bonutti et al. | 6,726,722 | B2 | 4/2004 | Walkenhorst et al. |
| 6,235,057 | B1 | 5/2001 | Roger et al. | 6,746,483 | B1 | 6/2004 | Bojarski et al. |
| 6,241,771 | B1 | 6/2001 | Gresser et al. | 6,755,836 | B1 | 6/2004 | Lewis |
| 6,245,081 | B1 | 6/2001 | Bowman et al. | 6,802,862 | B1 | 10/2004 | Roger et al. |
| 6,258,091 | B1 | 7/2001 | Sevrain et al. | 6,808,526 | B1 | 10/2004 | Magerl et al. |
| 6,269,716 | B1 | 8/2001 | Amis | 6,814,741 | B2 | 11/2004 | Bowman et al. |
| 6,270,518 | B1 | 8/2001 | Pedlick et al. | 6,830,572 | B2 | 12/2004 | McDevitt et al. |
| 6,273,890 | B1 | 8/2001 | Frazier | 6,852,125 | B2 * | 2/2005 | Simon et al. ............... 623/16.11 |
| 6,283,973 | B1 * | 9/2001 | Hubbard et al. ............... 606/104 | 6,863,671 | B1 | 3/2005 | Strobel et al. |
| 6,287,325 | B1 | 9/2001 | Bonutti | 6,872,040 | B2 | 3/2005 | Deeg et al. |
| 6,293,961 | B2 | 9/2001 | Schwartz et al. | 6,875,216 | B2 | 4/2005 | Wolf |
| 6,299,615 | B1 | 10/2001 | Huebner | 6,921,402 | B2 | 7/2005 | Contiliano et al. |
| 6,302,888 | B1 | 10/2001 | Mellinger et al. | 6,972,027 | B2 | 12/2005 | Fallin et al. |
| 6,306,159 | B1 | 10/2001 | Schwartz et al. | 6,989,034 | B2 | 1/2006 | Hammer et al. |
| 6,312,448 | B1 | 11/2001 | Bonutti | 2001/0051816 | A1 | 12/2001 | Enzerink et al. |
| 6,319,271 | B1 | 11/2001 | Schwartz et al. | 2002/0019649 | A1 | 2/2002 | Sikora et al. |
| 6,328,758 | B1 | 12/2001 | Tornier et al. | 2002/0058966 | A1 | 5/2002 | Tormala et al. |
| 6,342,060 | B1 | 1/2002 | Adams | 2002/0123752 | A1 | 9/2002 | Schultheiss et al. |
| 6,343,531 | B2 | 2/2002 | Amis | 2002/0169452 | A1 | 11/2002 | Tormala et al. |
| 6,368,322 | B1 | 4/2002 | Luks et al. | 2002/0169478 | A1 | 11/2002 | Schwartz et al. |
| 6,368,326 | B1 | 4/2002 | Dakin et al. | 2003/0009235 | A1 * | 1/2003 | Manrique et al. ............ 623/23.63 |

| | | | | | | |
|---|---|---|---|---|---|---|
| 2003/0032961 | A1 | 2/2003 | Pelo et al. | EP | 0441065 | 8/1991 |
| 2003/0033021 | A1 | 2/2003 | Plouhar et al. | EP | 0 490 417 A1 | 6/1992 |
| 2003/0033022 | A1 | 2/2003 | Plouhar et al. | EP | 0502698 | 9/1992 |
| 2003/0036797 | A1 | 2/2003 | Malaviya et al. | EP | 0 598 219 A2 | 5/1994 |
| 2003/0036801 | A1 | 2/2003 | Schwartz et al. | EP | 0651979 | 5/1995 |
| 2003/0078617 | A1 | 4/2003 | Schwartz et al. | EP | 0669110 | 8/1995 |
| 2003/0083662 | A1 | 5/2003 | Middleton | EP | 0686373 | 12/1995 |
| 2003/0088251 | A1 | 5/2003 | Braun et al. | EP | 0775473 | 5/1997 |
| 2003/0105477 | A1 | 6/2003 | Schwartz et al. | EP | 0 913 123 A1 | 5/1999 |
| 2003/0130694 | A1 | 7/2003 | Bojarski et al. | EP | 0913131 | 5/1999 |
| 2003/0135214 | A1 | 7/2003 | Fetto et al. | EP | 99121052.7 | 10/1999 |
| 2003/0152522 | A1 | 8/2003 | Miller et al. | EP | 99121106 | 10/1999 |
| 2003/0167072 | A1 | 9/2003 | Oberlander | EP | 0995409 | 4/2000 |
| 2003/0199878 | A1 * | 10/2003 | Pohjonen et al. ............... 606/73 | EP | 1 013 229 A2 | 6/2000 |
| 2003/0225459 | A1 | 12/2003 | Hammer et al. | EP | 1093773 | 4/2001 |
| 2004/0002734 | A1 | 1/2004 | Fallin et al. | EP | 1093774 | 4/2001 |
| 2004/0006345 | A1 | 1/2004 | Vlahos et al. | FR | 2622790 | 12/1989 |
| 2004/0006346 | A1 | 1/2004 | Holmen et al. | FR | 2688689 | 9/1993 |
| 2004/0015172 | A1 | 1/2004 | Biedermann et al. | FR | 2717070 | 9/1995 |
| 2004/0024456 | A1 | 2/2004 | Brown, Jr. et al. | FR | 2723528 | 2/1996 |
| 2004/0087981 | A1 | 5/2004 | Berube et al. | FR | 2744010 | 8/1997 |
| 2004/0122431 | A1 | 6/2004 | Biedermann et al. | FR | 2745999 | 9/1997 |
| 2004/0138664 | A1 | 7/2004 | Bowman | FR | 2770764 | 5/1999 |
| 2004/0138704 | A1 | 7/2004 | Gambale et al. | GB | 2 083 751 | 3/1982 |
| 2004/0143344 | A1 | 7/2004 | Malaviya et al. | GB | 2 118 474 | 11/1983 |
| 2004/0153103 | A1 | 8/2004 | Schwartz et al. | GB | 2 312 376 | 10/1997 |
| 2004/0166169 | A1 | 8/2004 | Malaviya | GB | GS 2312376 | 10/1997 |
| 2004/0220574 | A1 | 11/2004 | Pelo et al. | JP | 5362911 | 5/1978 |
| 2004/0225292 | A1 | 11/2004 | Sasso et al. | JP | 5362912 | 5/1978 |
| 2004/0243139 | A1 | 12/2004 | Lewis et al. | JP | 5374942 | 6/1978 |
| 2004/0267164 | A1 | 12/2004 | Rhodes et al. | JP | 5378230 | 6/1978 |
| 2004/0267265 | A1 | 12/2004 | Kyle | JP | 54-166092 | 11/1979 |
| 2004/0267270 | A1 | 12/2004 | Jacobs et al. | JP | 54-166093 | 11/1979 |
| 2004/0267276 | A1 | 12/2004 | Camino et al. | JP | 54-176284 | 12/1979 |
| 2004/0267277 | A1 | 12/2004 | Zannis et al. | JP | 54-178988 | 12/1979 |
| 2004/0267304 | A1 | 12/2004 | Zannis et al. | JP | 62-159647 | 7/1987 |
| 2005/0027307 | A1 | 2/2005 | Schwartz et al. | JP | 62-295657 | 12/1987 |
| 2005/0033363 | A1 | 2/2005 | Bojarski et al. | JP | 5269160 | 10/1993 |
| 2005/0074495 | A1 | 4/2005 | Schwartz et al. | JP | 7-51292 | 2/1995 |
| 2005/0090828 | A1 | 4/2005 | Alford | JP | 10-211213 | 8/1998 |
| 2005/0125073 | A1 | 6/2005 | Orban et al. | WO | WO 83/00615 | 3/1983 |
| 2005/0137600 | A1 | 6/2005 | Jacobs et al. | WO | WO 86/03666 | 12/1985 |
| 2005/0149033 | A1 | 7/2005 | McGuire et al. | WO | WO 87/01270 | 3/1987 |
| 2005/0159812 | A1 | 7/2005 | Dinger, III et al. | WO | WO 89/10096 | 11/1989 |
| 2005/0165482 | A1 | 7/2005 | Goldhahn et al. | WO | WO 93/15694 | 8/1993 |
| 2005/0177237 | A1 * | 8/2005 | Shappley et al. .......... 623/17.11 | WO | WO 95/02373 | 1/1995 |
| 2006/0030948 | A1 | 2/2006 | Manrique et al. | WO | WO 97/37603 | 10/1997 |
| 2006/0167482 | A1 | 7/2006 | Swain et al. | WO | WO 99/01084 | 1/1998 |
| 2006/0247642 | A1 | 11/2006 | Stone et al. | WO | WO 98/22047 | 5/1998 |
| 2006/0293709 | A1 | 12/2006 | Bojarski et al. | WO | WO 98/22048 | 5/1998 |
| 2007/0055255 | A1 | 3/2007 | Siegel | WO | WO-9822048 | 5/1998 |
| 2007/0078435 | A1 | 4/2007 | Stone et al. | WO | WO 99/12480 | 9/1998 |
| 2007/0083236 | A1 | 4/2007 | Sikora et al. | WO | WO-9901084 | 1/1999 |
| | | | | WO | WO 99/44544 | 9/1999 |
| | | | | WO | WO 00/40159 | 7/2000 |
| | | | | WO | WO 01/39671 A1 | 11/2000 |
| | | | | WO | WO 02/36020 A1 | 10/2001 |
| | | | | WO | WO 03/071962 A2 | 9/2003 |
| | | | | WO | WO 03/077772 A1 | 9/2003 |
| | | | | WO | WO 2005/104992 | 11/2005 |

FOREIGN PATENT DOCUMENTS

| | | |
|---|---|---|
| AU | 4402/66 | 10/1967 |
| AU | 22237/67 | 11/1968 |
| AU | 50285/69 | 8/1970 |
| AU | 58504/69 | 1/1971 |
| AU | 59638/69 | 2/1971 |
| AU | 15054/70 | 11/1971 |
| AU | 36151/71 | 5/1973 |
| AU | 43812/68 | 9/1973 |
| AU | A-71108/87 | 8/1987 |
| DE | 2919009 C2 | 11/1979 |
| DE | 3027138 | 3/1981 |
| DE | 3225620 A1 | 2/1983 |
| DE | 3136083 | 3/1983 |
| DE | 2333303 A1 | 2/1986 |
| DE | 4302397 | 7/1993 |
| DE | 29621340 | 5/1998 |
| DE | 19841252 | 3/2000 |
| EP | 0 108 912 A2 | 5/1984 |
| EP | 0 129 422 | 12/1984 |
| EP | 0 241 240 | 10/1987 |
| EP | 0 260 970 A2 | 3/1988 |
| EP | 0 315 371 A2 | 5/1989 |
| EP | 0 415 915 | 3/1991 |
| EP | 0440991 | 8/1991 |

OTHER PUBLICATIONS

A. Weiler, et al; Biodegradierbare Interferenzschrauben in der Kreuzbandchirurgie; OP-Journal 14 pp. 278-284; 1998.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Mark D. Miller et al.; "Pitfalls Associated with FasT-Fix Meniscal Repair," Arthroscopy: The Journal of Arthroscopic and Related Surgery, vol. 18, No. 8 (October), 2002: pp. 939-943.

Opus Medical; The AutoCuff System; www.opusmedical.com.; 2003.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

US 6,238,418, 05/2001, Schwartz et al. (withdrawn)

* cited by examiner

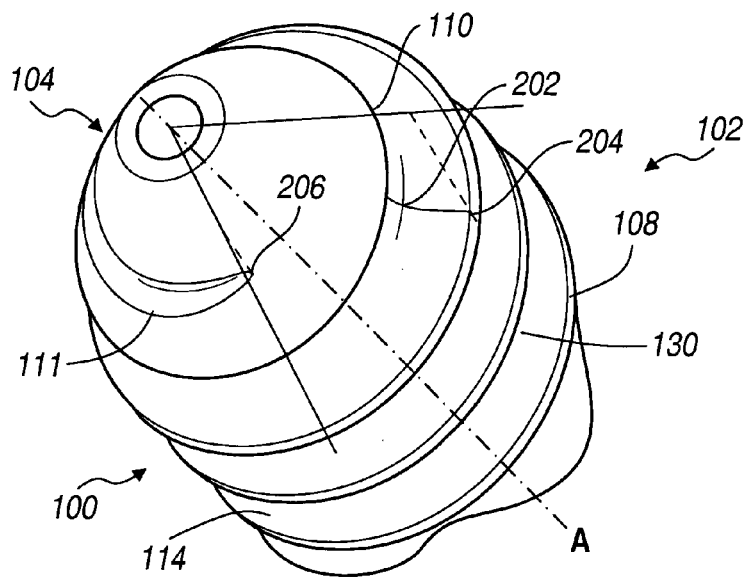
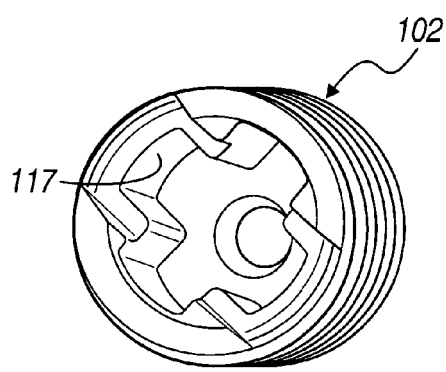
FIG. 3C
FIG. 3D
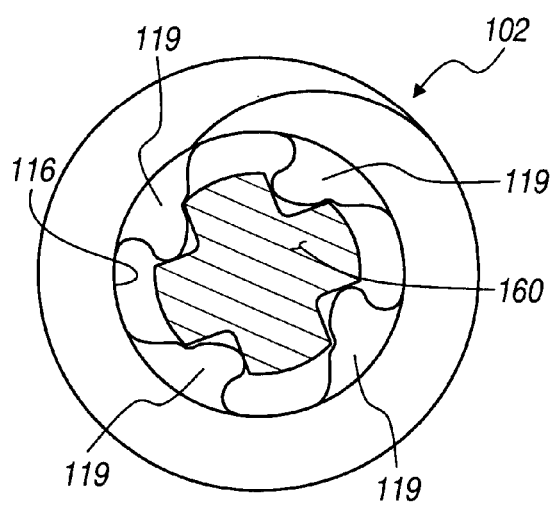
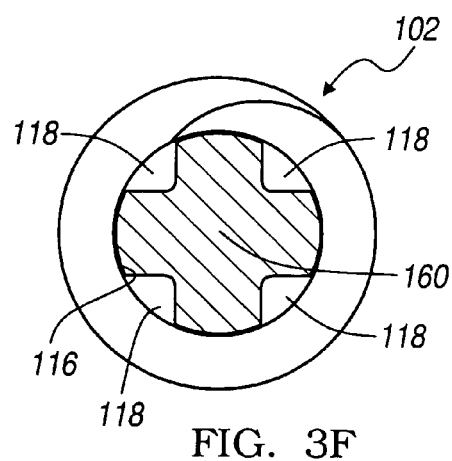
FIG. 3E
FIG. 3F

TISSUE FIXATION DEVICE

CROSS-REFERENCE TO RELATED APPLICATIONS

This application is a continuation-in-part of U.S. patent application Ser. No. 10/984,624 filed on Nov. 9, 2004. The disclosure of the above application is incorporated herein by reference.

INTRODUCTION

Various methods of attaching tissue, such as soft tissue, grafts or ligaments to bone are known. In anterior cruciate ligament reconstruction (ACL), for example, interference screws can be used to secure the graft against the walls of tunnels drilled in the tibia and the femur. The interference screws are wedged between the graft and a wall of the tunnel. To facilitate insertion and improve anchoring, some interference screws include cutting threads or other anchoring features.

SUMMARY

The present teachings provide a fixation device for securing tissue to a bone. The fixation device includes an anchor having a hollow body defining a longitudinal passage, and a plug configured to be received in at least a portion of the passage. The body comprises a cylindrical portion and a tapered tip portion. The cylindrical portion comprises a plurality of thin-walled window covers such that after implantation the window covers are resorbed first relative to other portions of the cylindrical portion for defining a plurality of apertures on the cylindrical portion.

The present teachings provide a fixation device for securing tissue to a bone and including an anchor having a hollow body defining a longitudinal passage. The body comprising portions of varying rates of resorption such that, after implantation, a plurality of apertures are formed by resorption through an outer surface of the body before resorption of other portions of the anchor.

The present teachings provide a method for securing tissue to a bone. The method includes forming a tunnel in the bone, passing the tissue through the tunnel, providing a cannulated anchor defining a longitudinal passage, implanting the cannulated anchor between the tissue and the tunnel, and resorbing portions of the implanted anchor for defining apertures through an outer surface of the anchor.

The present teachings also provide a method for repairing a defect in tissue. The method includes providing an anchor defining a longitudinal passage, implanting the anchor through the defect, and resorbing portions of the implanted anchor for defining apertures through an outer surface of the anchor before resorbing other portions of the anchor.

The present teachings also provide a fixation device for securing tissue to a bone or repairing tissue. The fixation device includes an anchor having an anchor body. The anchor body is substantially defined by a plurality of longitudinal ribs positioned to define a hollow interior passage, and a thread extending about the plurality of longitudinal ribs.

Further areas of applicability of the present invention will become apparent from the detailed description provided hereinafter. It should be understood that the detailed description and specific examples, while indicating various aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3C is a perspective view of an anchor for a fixation device according to the present teachings;

FIG. 3D is a perspective view of an anchor for a fixation device according to the present teachings;

FIG. 3E is an end view of an anchor for a fixation device according to the present teachings shown coupled with an insertion driver;

FIG. 3F is an end view of an anchor for a fixation device according to the present teachings shown coupled with an insertion driver;

DESCRIPTION OF VARIOUS ASPECTS

The following description is merely exemplary in nature and is in no way intended to limit the invention, its application, or uses. For example, although the devices and methods of the invention are illustrated for use in anterior cruciate ligament reconstruction (ACL) in knee surgery, use for securing any soft tissue, hard tissue, bone cartilage, ligament, natural or artificial graft, such as, for example, polylactide (PLA), polyglolide (PGA), polyurethane urea, and other grafts, to a bone is contemplated.

Figure 1:
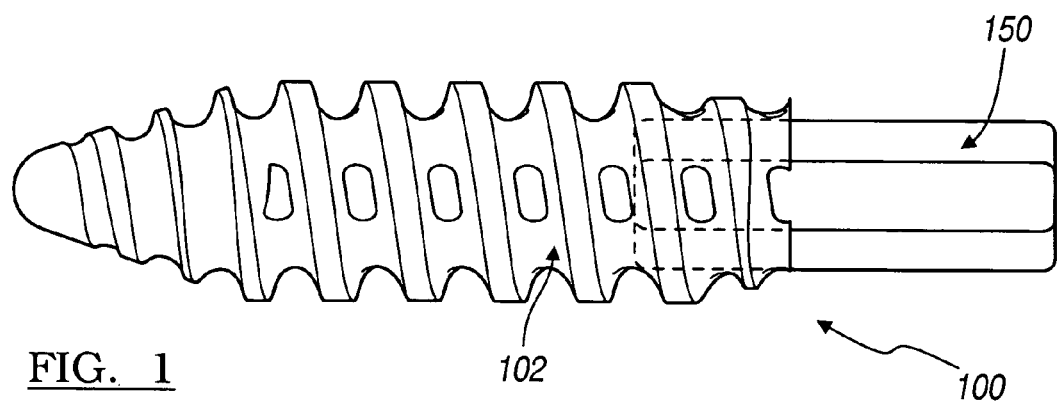
FIG. 1 is a partially assembled perspective view of a fixation device according to the present teachings.

Referring to FIG. 1, an exemplary fixation device 100 according to the present teachings includes a cannulated anchor 102 and a plug 150 that can be received in the anchor 102. FIGS. 2-5 illustrate exemplary anchors 102 and plugs 150. The cannulated anchor 102 includes a cylindrical portion 106 and a tapered tip portion 104. The anchor 102 can be threaded. The cylindrical portion 106 can have threads 114 with pitch $p_1$, and the tapered tip portion 104 can have threads 110 with a different pitch $p_2$. For an exemplary 30 mm long anchor, for example, $p_1$ can be about 2.2 mm and $p_2$ about 1.8 mm, or the other way around, or other values can be used for these dimensions. The threads 114, 110 of both portions 106, 104 can have "blunt" edges that are herein defined as non-cutting edges 108. The pitch $p_2$ of the tapered tip portion 104 can be selected, for example, to facilitate the insertion of the anchor 102 while using only non-cutting edges 108 and avoiding the need for sharp or cutting edges.

Figure 2:
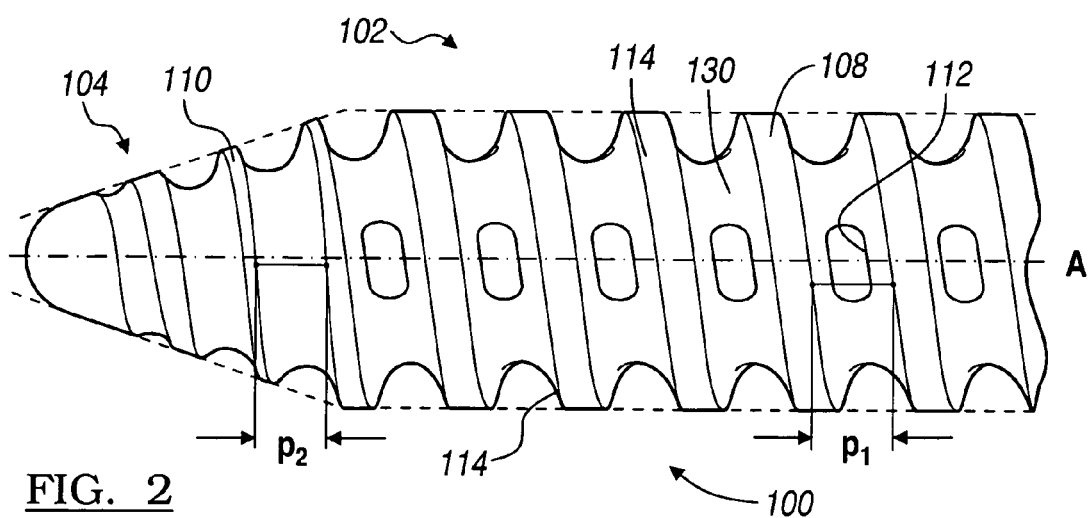
FIG. 2 is a perspective view of an anchor for a fixation device according to the present teachings.
Figure 2A:
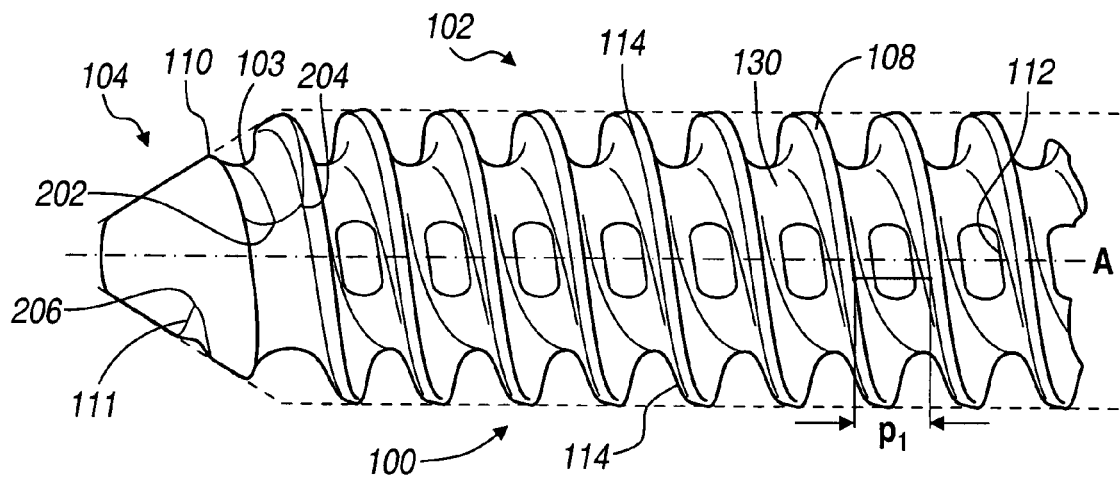
FIG. 2A is a perspective view of an anchor for a fixation device according to the present teachings.
Figure 2B:
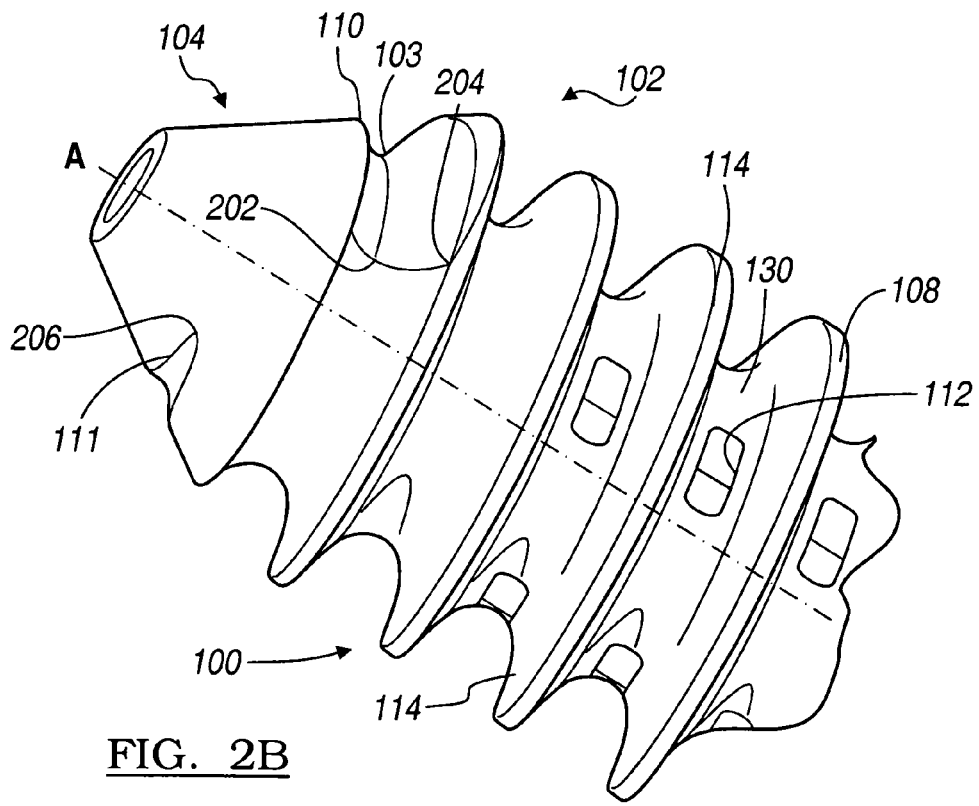
FIG. 2B is a perspective view of an anchor for a fixation device according to the present teachings.
Figure 2C:
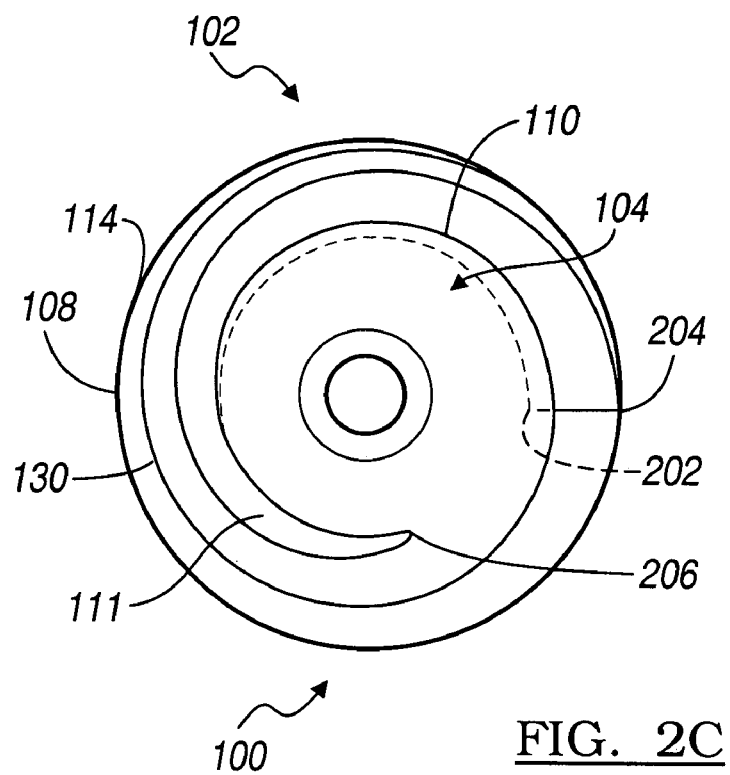
FIG. 2C is an end view of the anchor of FIG. 2B.

Referring to FIGS. 2A, 2B and 2C, the tapered tip portion 104 can include a partial/incomplete winding 111 (i.e. less than one winding) that extends less than one complete turn or winding (less than 360 degrees) around the tapered tip 104. The incomplete winding 111 can start, for example, at location 206 and terminate at locations 202, 204 having a rotation of about 300-degrees from the starting location 206. In this manner, the incomplete winding 111 reaches both the maximum diameter of the thread 110 and the maximum diameter of the root 103 of the thread 110 in less than one winding or about 300-degrees in the tapered tip portion 104. The incomplete winding 111 in synergy with the non-cutting edges 108 throughout the threads 114, 110 can further facilitate a gradual and controlled insertion of the anchor 102, thereby reducing damage to surrounding tissue. The incomplete winding 111 is also illustrated in FIGS. 3B and 3C, discussed below.

Figure 8:
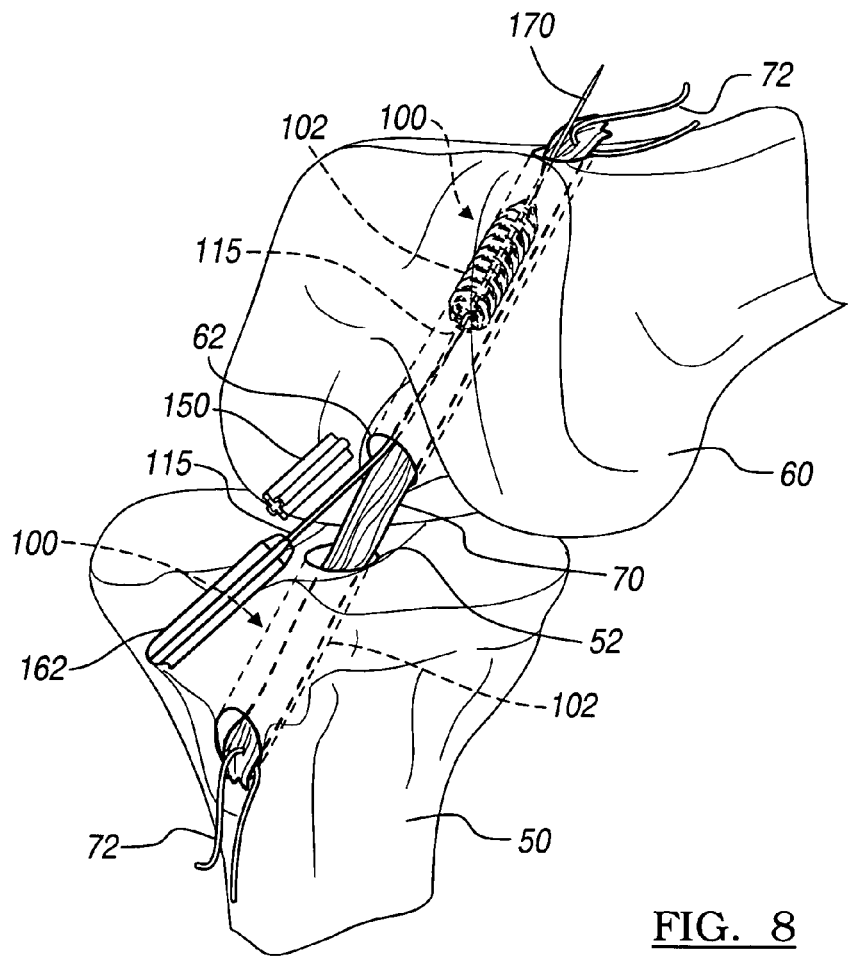
FIG. 8 is an environmental view of a fixation device according to the present teachings.

Referring to FIG. 8, the shape of the tapered tip portion 104 together with the smaller pitch threads 110 or partial thread 111 facilitates the insertion of the anchor 102 into a bone tunnel 62 to wedge a ligament or graft 70 against the wall of the tunnel 62 by pushing apart, without cutting into, surrounding tissues, including both bone and soft tissue graft. The threads 114 of the cylindrical portion 106 can also push apart, without cutting into, surrounding tissue, and do not follow any paths that may be opened by the pushing apart action of the threads 110 of the tapered tip portion 104. The anchor 102 can be made of any biocompatible material, including metal, such as titanium, for example. The anchor 102 can also be made of bioabsorbable/resorbable material, such as Lactosorb® from Biomet, Inc., Warsaw, Ind., for example.

Figure 3:
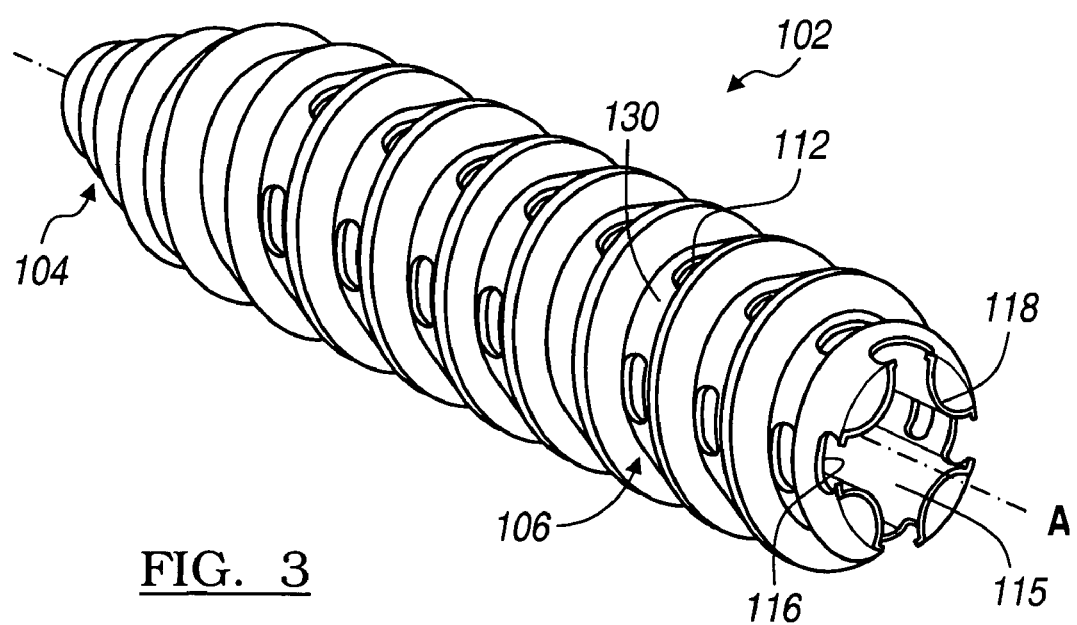
FIG. 3 is a perspective view of an anchor for a fixation device according to the present teachings.
Figure 3A:
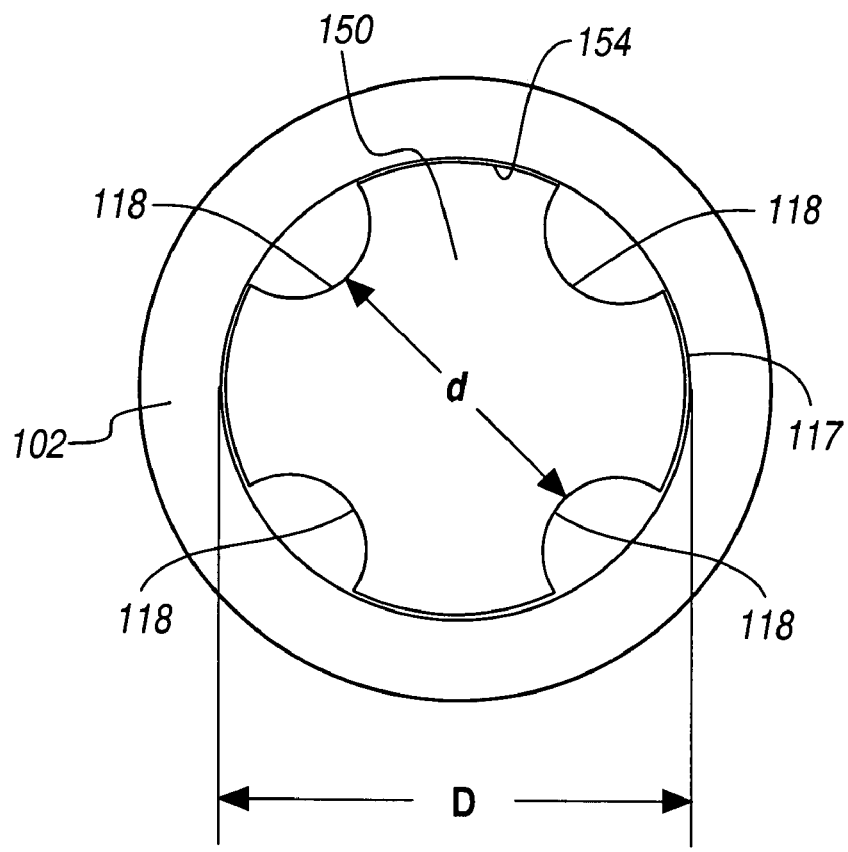
FIG. 3A is a cross-sectional view of a cannulated anchor with a plug inserted therein for a fixation device according to the present teachings.
Figure 3B:
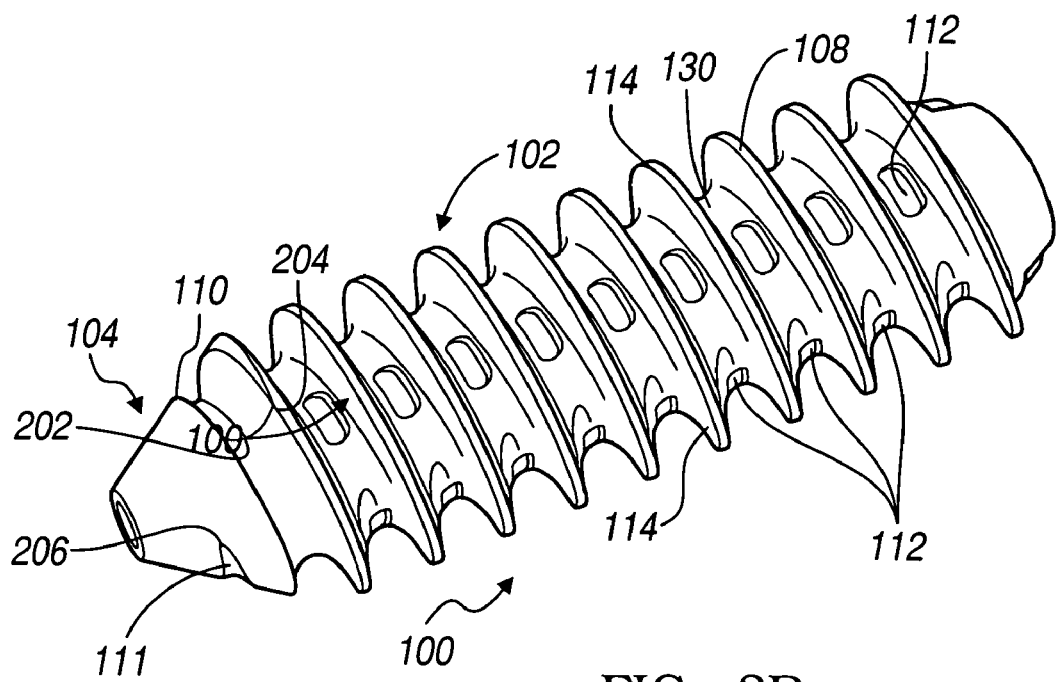
FIG. 3B is a perspective view of an anchor for a fixation device according to the present teachings.
Figure 4:
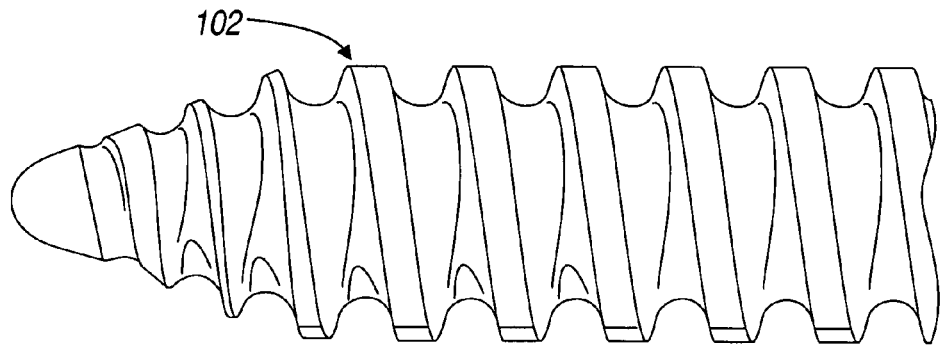
FIG. 4 is a perspective view of an anchor for a fixation device according to the present teachings.
Figure 4A:
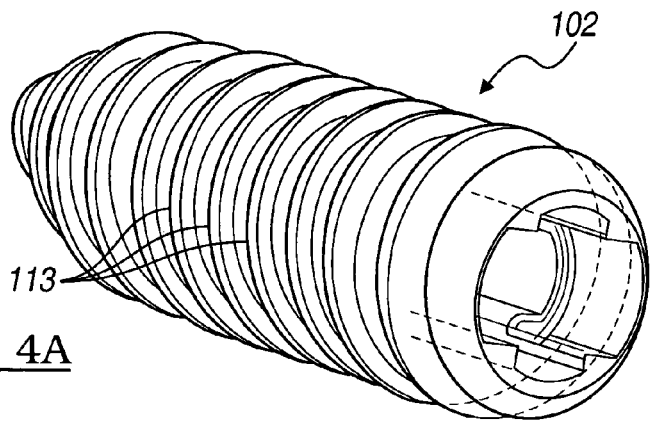
FIG. 4A is a perspective view of an anchor for a fixation device according to the present teachings.
Figure 4B:
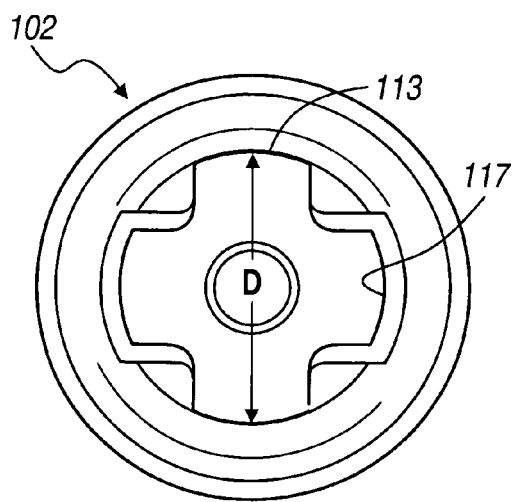
FIG. 4B is an end view of the anchor of FIG. 4A.
Figure 4C:
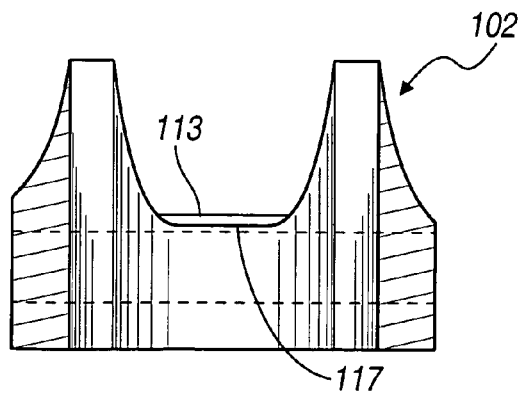
FIG. 4C is a partial side view of the anchor of FIG. 4A.
Figure 4D:
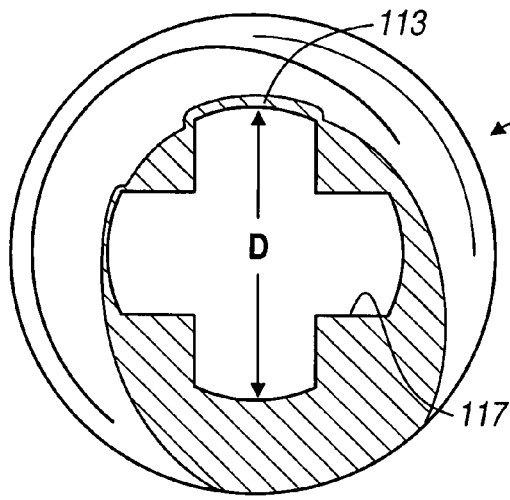
FIG. 4D a cross-sectional view of the anchor of FIG. 4A.
Figure 4E:
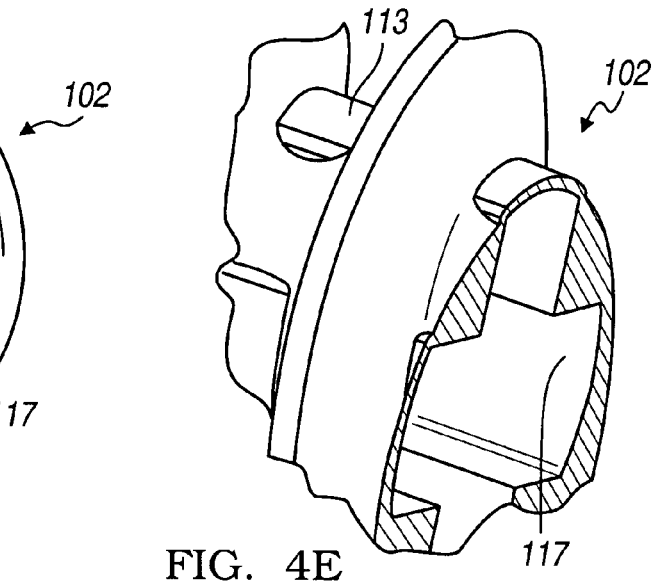
FIG. 4E a detail of the anchor of FIG. 4A.
Figure 5:
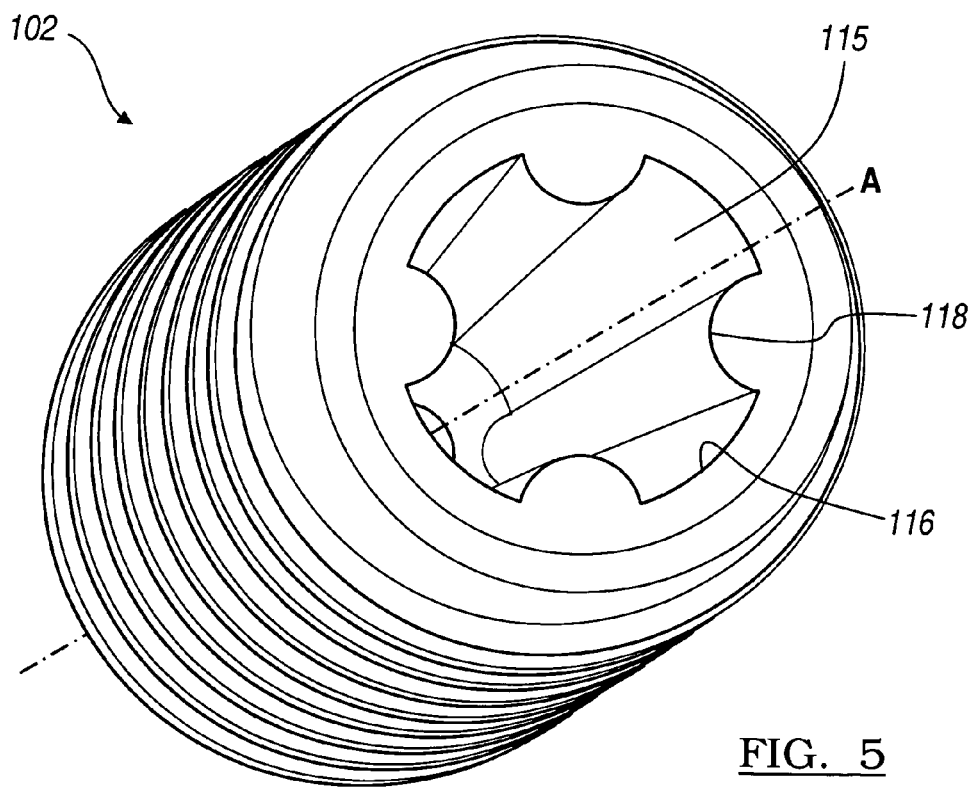
FIG. 5 is a perspective view of an anchor for a fixation device according to the present teachings.
Figure 6:
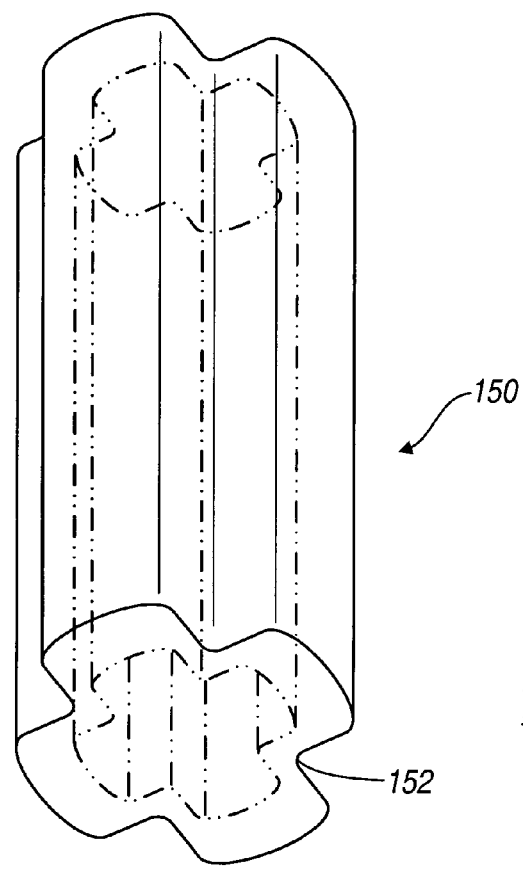
FIG. 6 is a perspective view of a plug for a fixation device according to the present teachings.

Referring to FIGS. 3, 3A-F, 5 and 6, the cannulated body of the anchor 102 defines a longitudinal passage 115 that extends throughout the entire body of the anchor 102 along a longitudinal center axis "A". A plug-receiving portion 116 of the longitudinal passage 115 extends along the cylindrical portion 106 of the anchor and can have an enlarged opening of a shape, such as a cruciate shape defined by four longitudinal ribs 118, or any other shape, such as a fingered shape, a hexagonal, pentagonal, triangular or other polygonal or curvilinear shape. In one aspect, the plug-receiving portion 116 can include asymmetric lobes 119 defining an asymmetric opening for the passage 115, such that the same size insertion tool or driver 160 can be used for different size anchors 102, as illustrated in FIGS. 3E and 3F. For example, the driver 160 can substantially occupy the cruciate cross-section of the plug-receiving portion 116 of the anchor 102 and conform substantially with the entire profile of the ribs 118, as illustrated in FIG. 3F. The same driver 160 can be used with a larger anchor 102, as illustrated in FIG. 3E, such that the driver 160 can be captured by the end portions of the asymmetric lobes 119 without substantially occupying the entire cross-section of the plug-receiving portion 116.

The plug 150 can have a shape that is complementary to the shape of the plug-receiving portion 116. For example, for the cruciate shape the plug 150 can have grooves 152 shaped for mating with the ribs 118 (or lobes 119) when the plug 150 is inserted into the passage 115. The plug 150 can be made of osteoinductive and/or osteoconductive material to promote bone growth through the anchor 102. The material of the plug 150 can be, for example, calcium phosphate, calcium sulfate, tricalcium phosphate, allograft bone, autograft bone, demineralized bone matrix, coral material, combinations thereof, etc. The plug can also be made from ProOsteon, available from Interpore Cross International, Irvine, Calif. The plug 150 can also be cannulated for engaging an insertion tool, and/or for facilitating tissue growth and/or injecting biologic agents therethrough.

Referring to FIGS. 2 and 3, the outer surface 130 of the cylindrical portion 106 of the anchor 102 between the threads 114 can include apertures 112. The apertures 112 can be formed, for example, by cutting through, from the inside to the outside, the outer surface 130 of the anchor 102 between the threads 114, using a cutting instrument that can be received in the anchor 102, although other cutting methods can also be used. The apertures 112 can also be formed not by cutting, but by using an appropriate insert/plug during the molding process of the anchor 102. The apertures 112 can, therefore, be arranged along the direction of the longitudinal axis A between adjacent threads 114 of the cylindrical portion 106. The apertures 112 can extend substantially between the threads 114 and ribs 118, occupying the entire wall-less region therebetween. The size of the apertures 112 can be selected to occupy only a portion of the outer surface 130 between the threads 114 and the ribs, as illustrated in FIG. 2.

Referring to FIG. 3, in one aspect, the size of the apertures 112 can be selected to occupy the entire portion of the outer surface 130 between the threads 114 and the ribs 118. In this respect, the structural integrity of the cylindrical portion 106 of the anchor 102 can be provided by the threads 114 and the ribs 118, which together form an open structural framework with no material wall therebetween. In this manner, the anchor 102 is molded as a rib/thread framework that does not include any wall structures therebetween, the apertures 112 defined by the absence of such wall material. The apertures 112 can facilitate bone ingrowth or outgrowth through the anchor 102 and can also be used to distribute a biologic material, including osteoinductive/osteoconductive material, such as calcium phosphate, platelet concentrates, fibrin, etc., which may be injected through the passage 115. The plug 150, in addition to providing bone growth promoting benefits, closes the longitudinal passage 115 and can substantially prevent such material from draining out through the apertures 112.

Referring to FIG. 3A, the outer surface 154 of the plug 150 can be shaped to extend outward beyond a minor diameter "d" defined by the ribs 118. The outer surface 154 of the plug can mate with an interior surface 117 of the anchor 102 at a major diameter "D" of the interior surface 117 at which the apertures 112 are formed, such that portions of the plug 150 can contact tissue through the apertures 112 when the anchor 102 is implanted, thereby promoting tissue growth and better tissue attachment.

Referring to FIGS. 4, 4A-4E, and 5, the cylindrical portion 106 of the anchor can also be solid, without any apertures. In particular, the cylindrical portion 106 can be formed to include a plurality of thin-walled window covers 113, which, because of their reduced dimensions, can quickly be resorbed after implantation of the anchor 102. Accordingly, the window covers 113 are resorbed at a different rate and preferentially relative to other portions of the cylindrical portion 106, thereby defining a plurality of apertures 112, similar to the apertures 112 described above in connection with FIGS. 2 and 3, and providing similar growth promoting properties. Including the window covers 113 in the anchor 102 can simplify the manufacturing process for the anchor 102. For example, any special precautions for keeping the plurality of apertures 112 open during molding are no longer necessary when window covers 113 provided. The presence of window covers 113 during the insertion of the anchor 102 can facilitate the insertion of the anchor 102 by reducing friction and the associated insertion torque. Similarly to the apertures 112, the window covers 113 can extend between adjacent threads 114 of the cylindrical portion 106, substantially parallel to the threads 114 in the regions between adjacent ribs 118. After resorption, the window covers 113 define apertures substantially similar to the pre-formed apertures 112 of the anchors 102 illustrated in FIG. 1, 2 or 3.

Figure 7A:
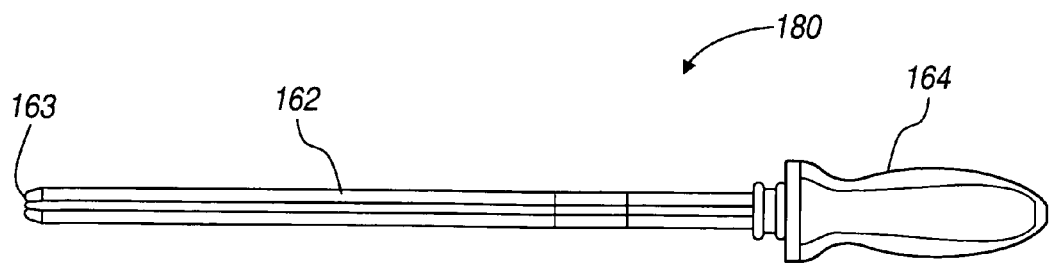
FIG. 7A is a perspective view of a driver for use with a fixation device according to the present teachings.

Referring to FIG. 7A, an exemplary driver 180 that can be used to rotate the anchor 102 and facilitate its insertion is illustrated. The driver 180 can include a handle 164 and a suitably shaped shaft 162 for engaging the plug-receiving portion 116 of the passage 115 of the anchor 102. The handle 164 can be modularly connected to the shaft 162. Alternatively, the plug 150 can be pre-inserted into the anchor 102 and the driver 180 can engage the cannulated plug 150. The driver 180 can also be cannulated. The shaft 162 can have a cruciate shape or any other shape that can engage the plug-receiving portion 116 and can terminate at a tapered end 163.

Figure 7B:
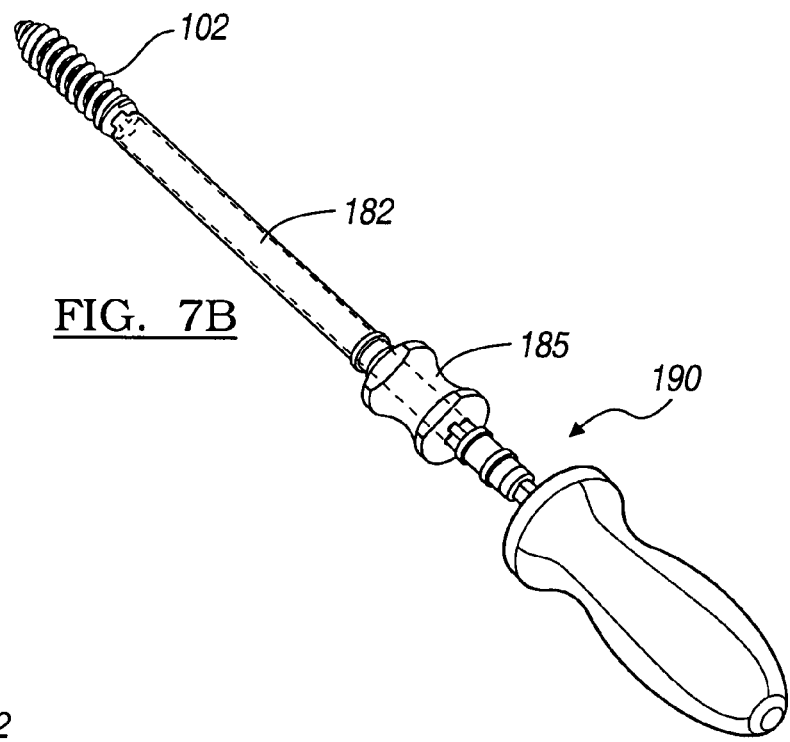
FIG. 7B is a perspective view of an inserter assembly shown coupled with a fixation device according to the present teachings.
Figure 7C:
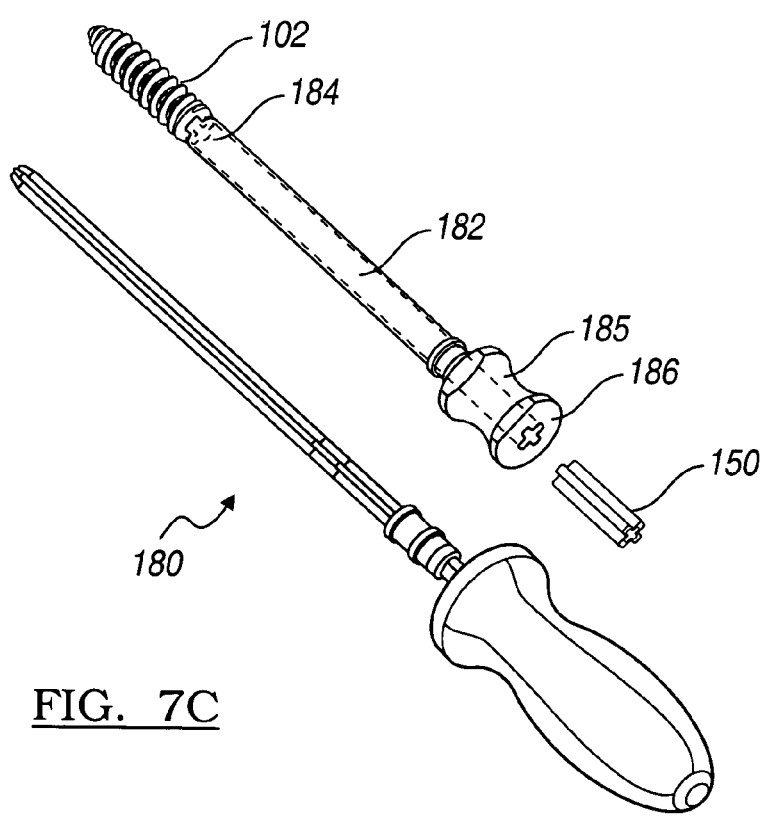
FIG. 7C is an exploded view of an inserter assembly shown with a fixation device according to the present teachings.
Figure 7D:
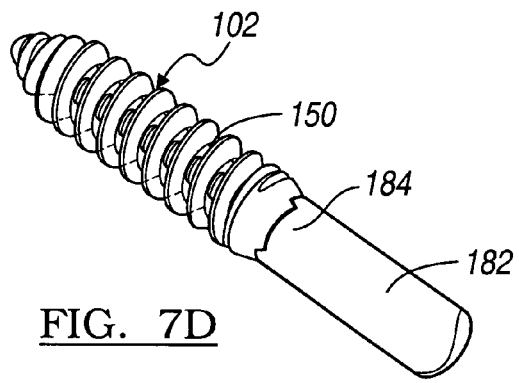
FIG. 7D is a perspective view of the fixation device of FIG. 7C shown with a sleeve of the inserter assembly attached thereon.
Figure 7E:
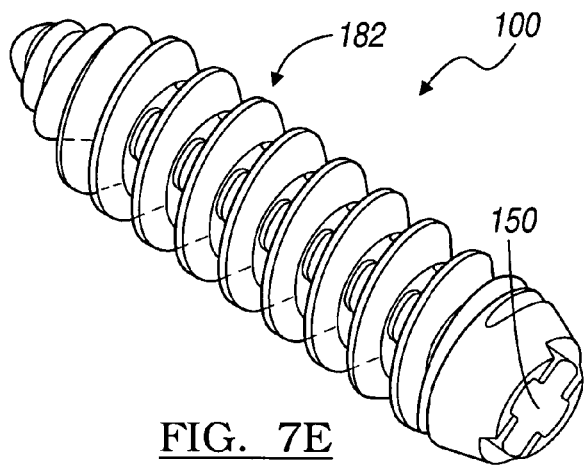
FIG. 7E is a perspective view of the fixation device of FIG. 7D shown after the inserter assembly is removed.

Referring to FIGS. 7A-7C, and FIG. 8A, an inserter assembly 190 for facilitating the insertion of the anchor 102 and plug 150 is illustrated. The inserter assembly 190 can include the driver 180 described above, and an anchor sleeve 182. The driver 180 can be used to apply torque to the interior surface 117 of the anchor 102 to insert the anchor 102 into the implantation site. The driver 180 can pass through the anchor sleeve 182 to engage the anchor 102, as illustrated in FIG. 7B. The anchor sleeve 182 can have a distal end 184, which can be two-pronged or otherwise configured to mate or engage proximally of the anchor 102, and a tubular element 185 modularly or integrally coupled to the proximal end 186 of the sleeve 182. After the anchor 102 is inserted in the desired location, the driver 180 can be removed from the anchor sleeve 182, and the anchor sleeve 182 can remain engaged with the anchor 102, as illustrated in FIG. 7C. The plug 150 can be inserted from the proximal end 186 of the anchor sleeve 182. The driver 180 can be re-inserted into the proximal end 186 of the anchor sleeve 182 through the tubular element 185. A pusher or other driver tool can be used for forcing the plug 150 through the anchor sleeve 182 and into the plug-receiving portion 116 of the anchor 102, as illustrated in FIG. 7C. The plug 150 can be secured by interference fit into the anchor 102. After the plug 150 is fully seated within the anchor 102, as illustrated in FIG. 7D, the anchor sleeve 182 can be disengaged from the anchor 102 by axial pulling, and completely removed, as illustrated in FIG. 7E.

Referring to FIG. 8, an exemplary, but not limiting, use of the fixation device 100 is illustrated in the context of arthroscopic knee surgery. A ligament or graft 70 passes through a tibial tunnel 52 and a femoral tunnel 62 and is fixed in the tibia 50 and femur 60 with sutures 72. The fixation device 100 can be implanted in the tibial tunnel 52 or in the femoral tunnel 62, or two fixation devices 100 can be implanted, one in each tunnel 52, 62. A guide wire 170 can be inserted between the wall of tibial tunnel 52 and/or femoral tunnel 62 and the graft 70 to guide the anchor 102 of the fixation device 100, as needed. The anchor 102 can be passed over the guide wire 170 and wedged between the graft 70 and the tibial tunnel 52 and/or femoral tunnel 62 by rotation using the cannulated driver 160. The guide wire 170 can then removed. The passage 115 can be closed by inserting the plug 150. The inserter assembly 190 can be used for inserting the anchor 102 and the plug 150, as described in connection with FIGS. 7A-E above.

Figure 8A:
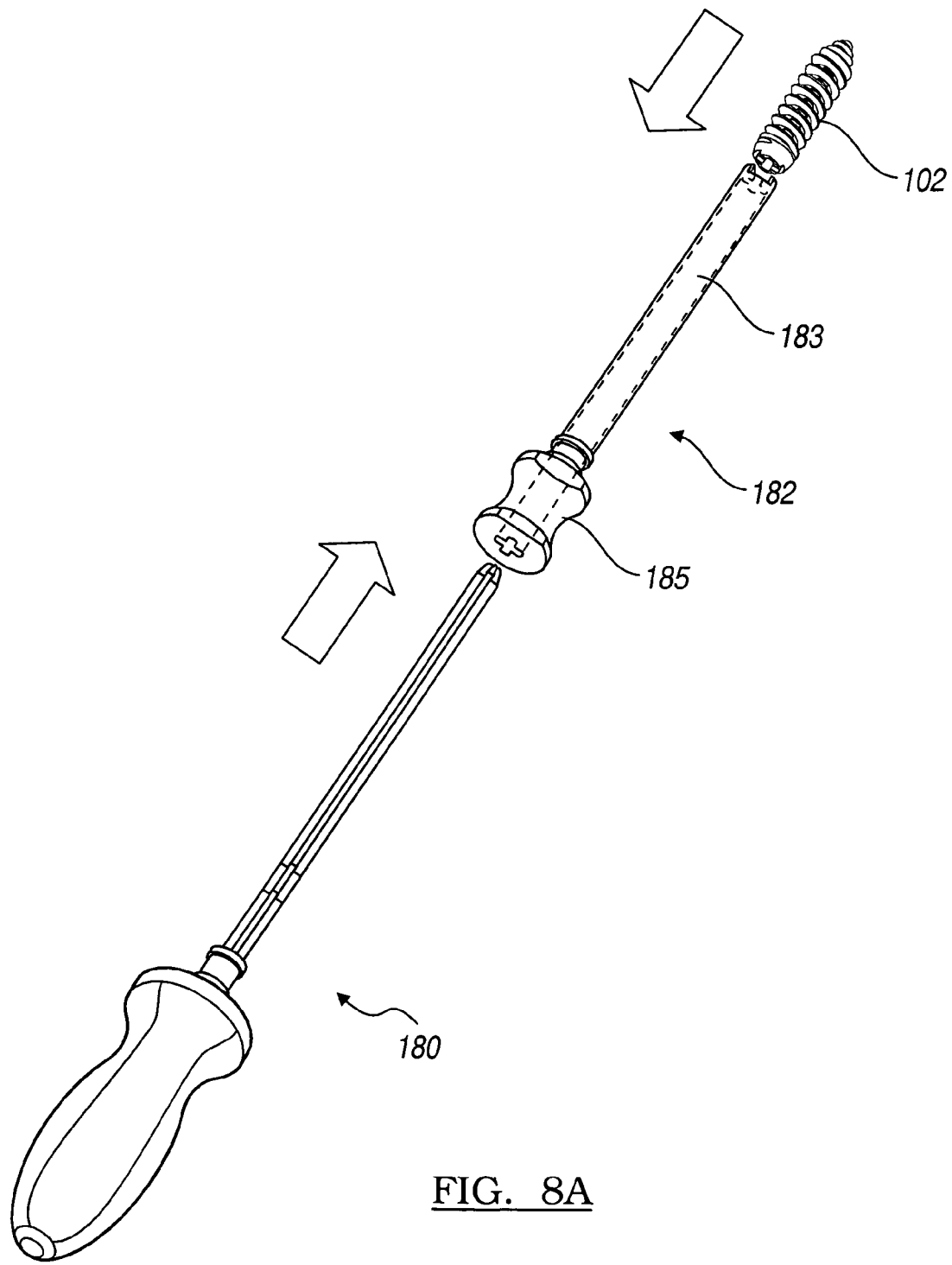
FIGS. 8A through 8F illustrate aspects of implanting a fixation device according to the present teachings.
Figure 8B:
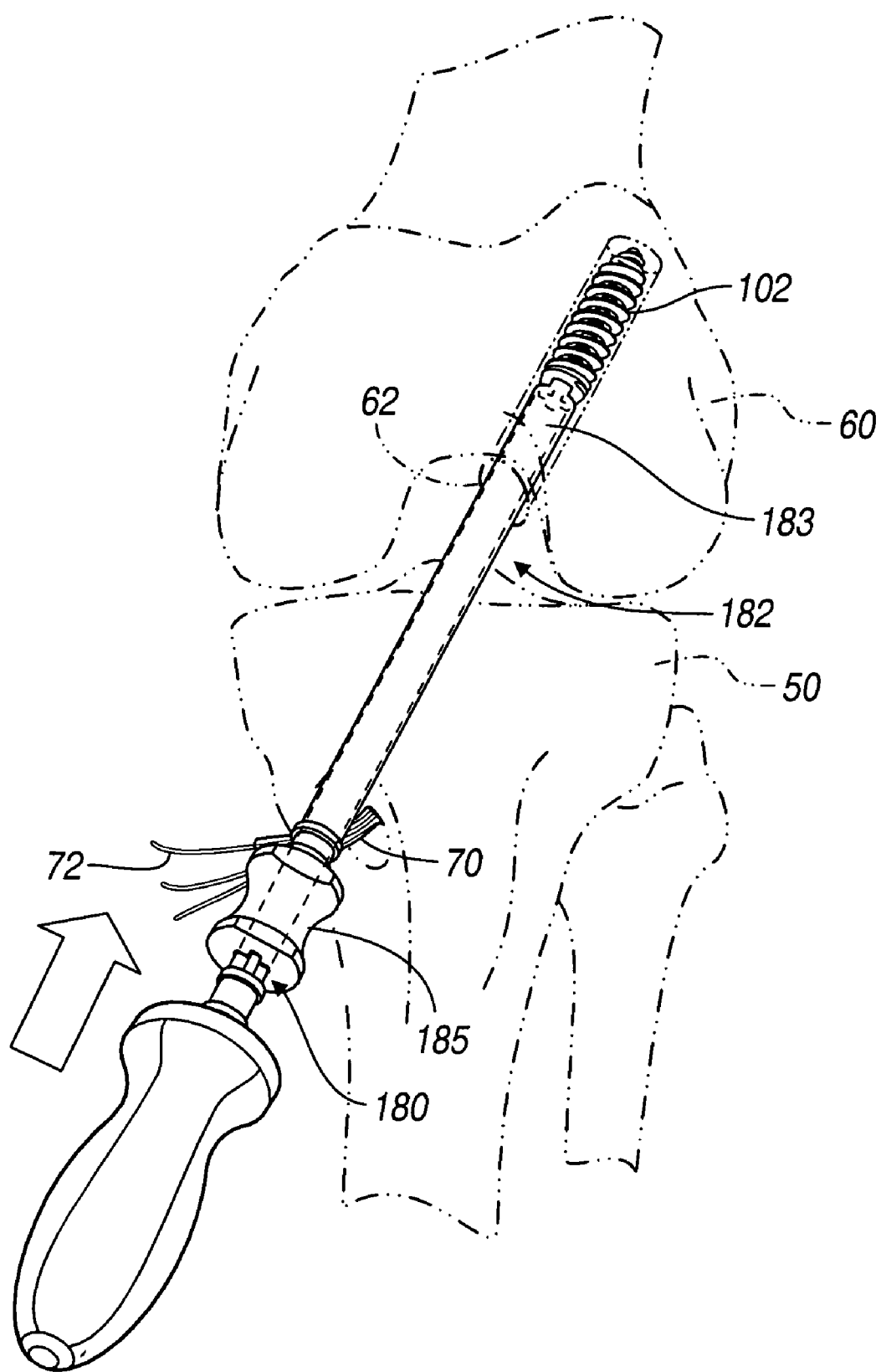
Figure 8C:
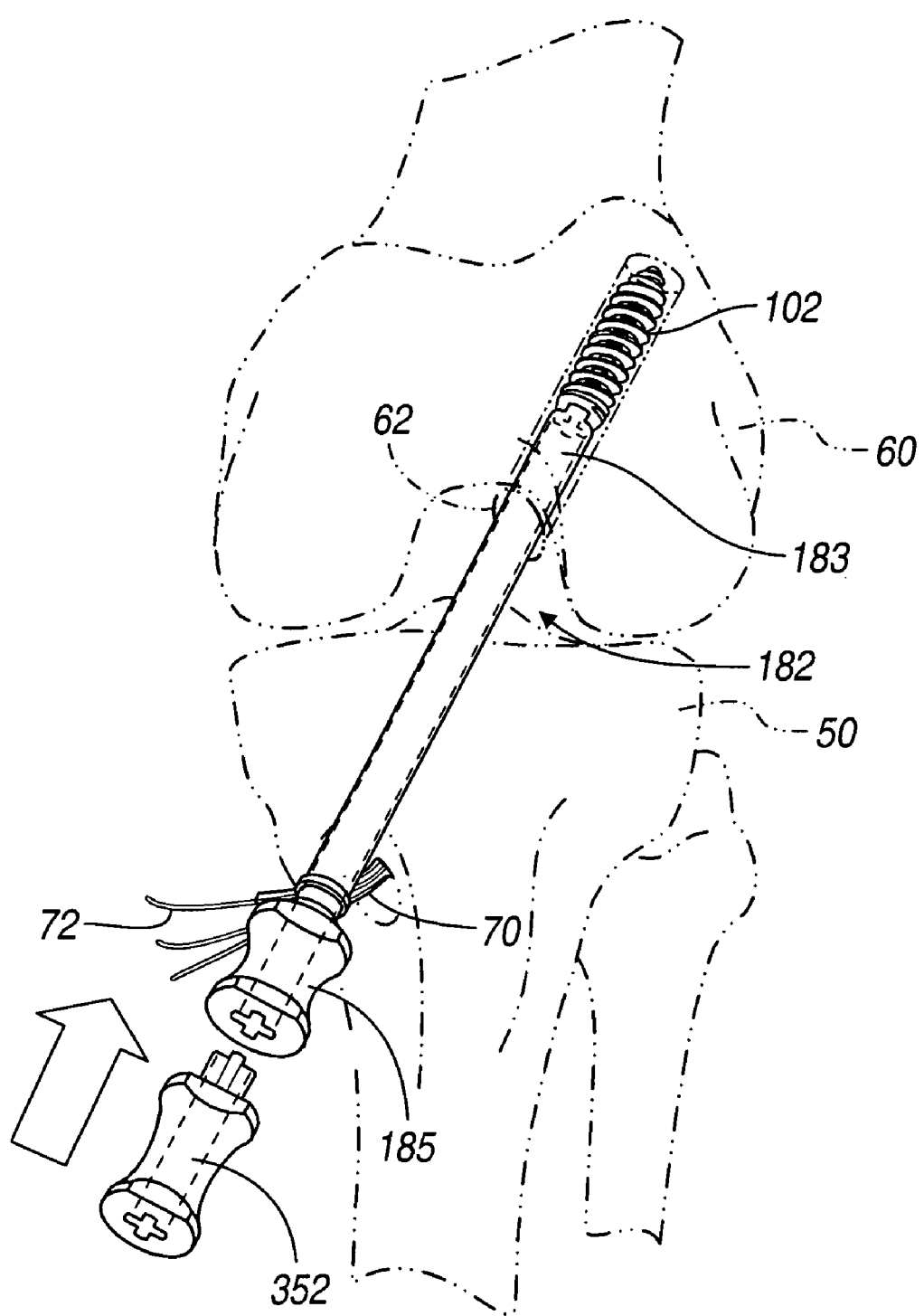
Figure 8D:
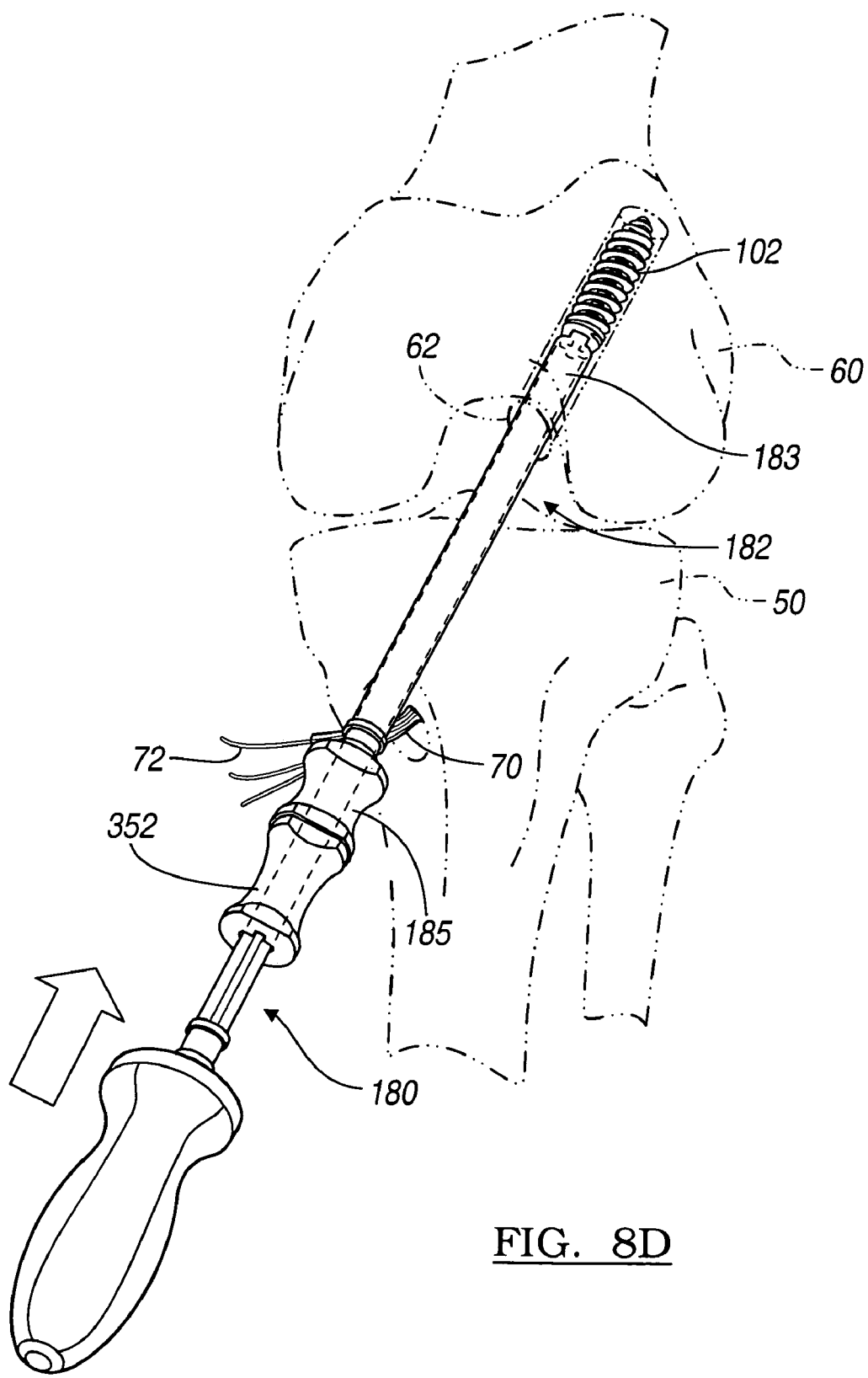
Figure 8E:
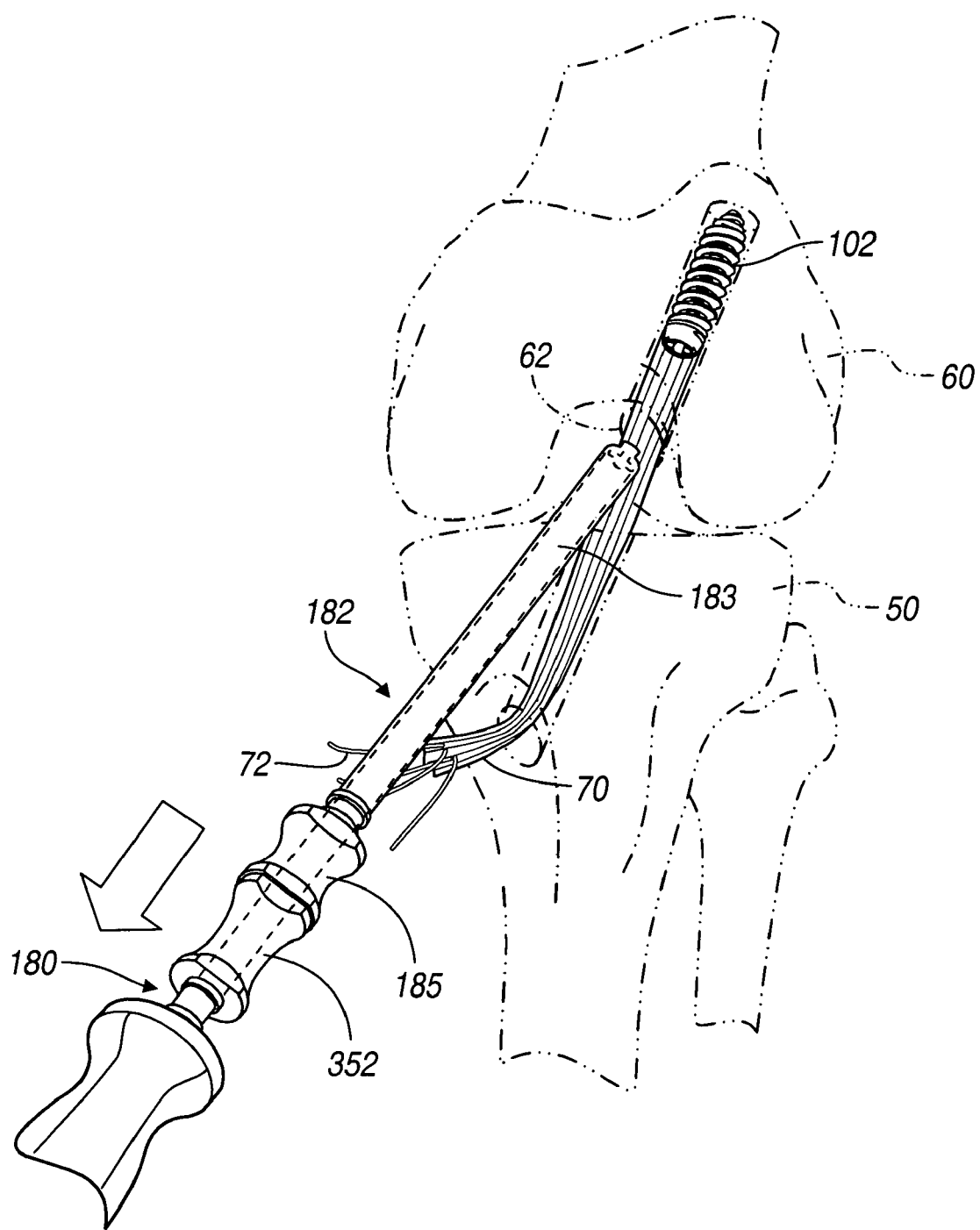
Figure 8F:
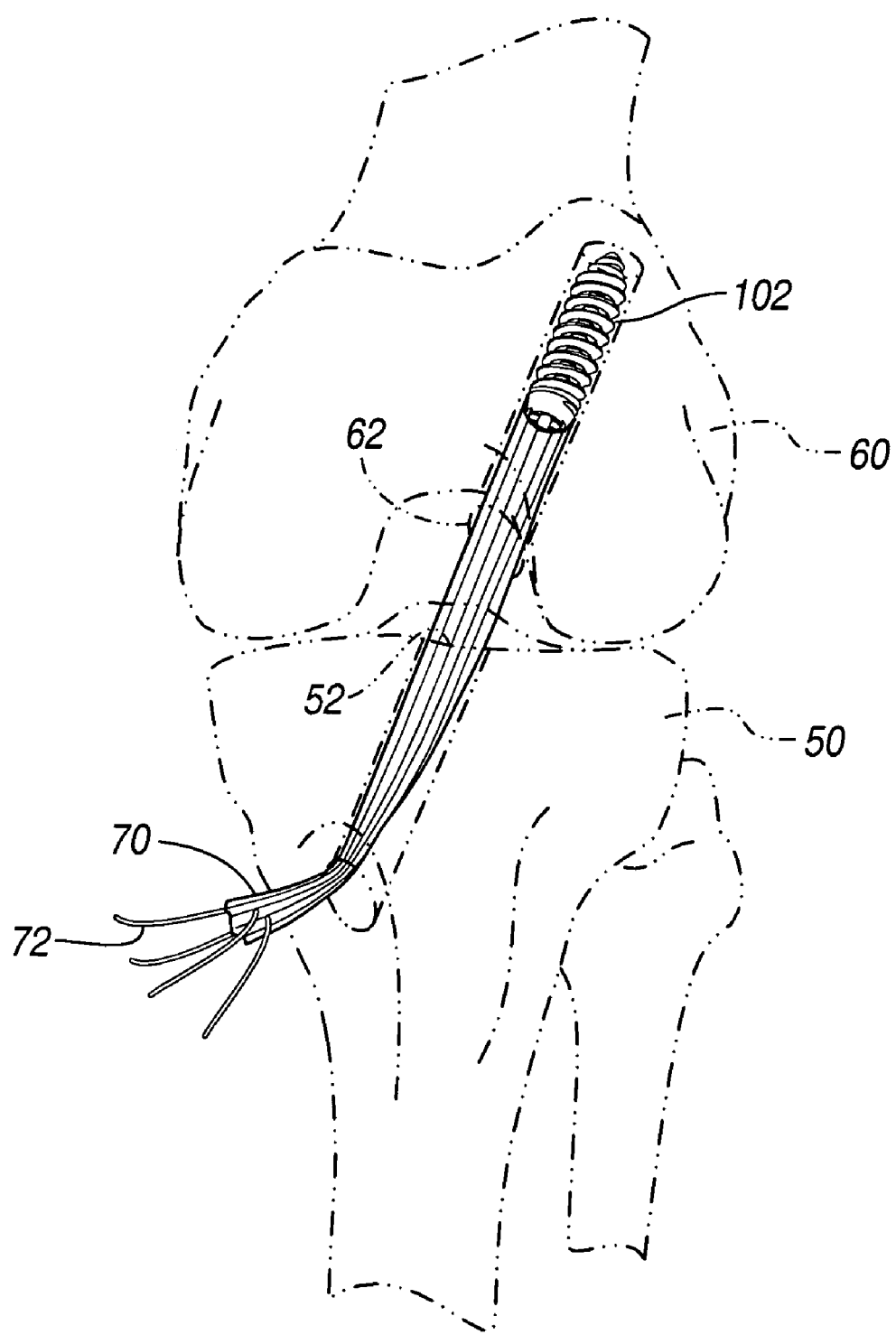

Referring to FIGS. 8A-8F, a single anchor 102 can be inserted in the femoral tunnel 62, after the graft 70 has been seated. Referring to FIG. 8A, the driver 180 can be inserted through the sleeve 182 into the anchor 102 for engaging the anchor 102 as described above. The driver 180, coupled with the sleeve 182, can be used to implant the anchor 102 into the femoral tunnel 62, as illustrated in FIG. 8B. The driver 180 can then be removed, and a plug sleeve 352 similar to the tubular element 185 of the anchor sleeve 182, can be coupled to the anchor sleeve 182, as illustrated in FIG. 8C. The plug sleeve 352 can be cannulated and have a cruciate shape for matingly receiving the cruciate-shaped plug 150. The plug 150 or other biological material can be inserted through the plug sleeve 352 and pushed into the passage 115 of the anchor 102 using the driver 180 or other pusher tool, as illustrated in FIG. 8D. The driver 180 and the sleeve 182 can be disengaged from the anchor 102 and removed, as illustrated in FIG. 8E, leaving the anchor 102 in the femoral tunnel 62 engaging the graft 70, as illustrated in FIG. 8F.

Osteoinductive/conductive material can be optionally injected through the passage 115 of the anchor 102 using, for example, the cannulated driver 160, a syringe, a pump or other suitable delivery device before inserting the plug 150. Alternatively, osteoinductive/conductive material can be used to form the plug 150 which can be pushed into the passage 115 of the anchor 102.

Figure 9:
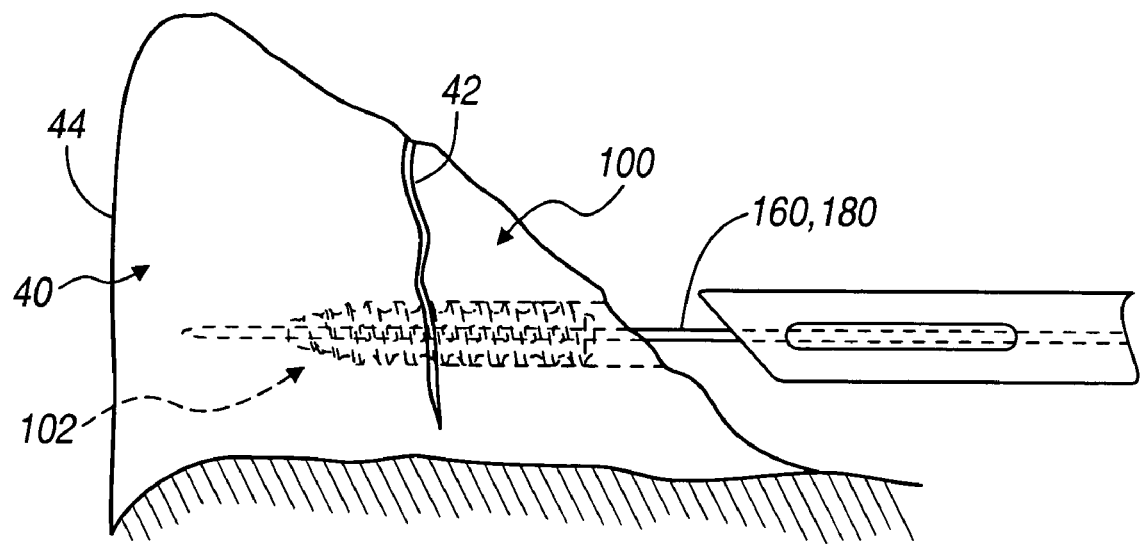
FIG. 9 is an environmental view of a fixation device according to the present teachings.

Referring to FIG. 9, another exemplary use of the fixation device 100 is illustrated in the context of soft tissue repair, such as repairing a meniscus 40 having a tear or other defect 42. The cannulated anchor 102 can be inserted through the defect 42 using an insertion tool, such as drivers 160, 180 as described above. A core, such as a solid or cannulated plug similar to the plug 150 illustrated in FIG. 6, can also be optionally inserted into the passage 115 of the anchor 102. The core can also be in the form of a gel or other biocompatible material, and may have properties promoting tissue growth. The anchor 102 can also be guided through and past the defect 42 such that the anchor exits completely through a back surface 44 of the meniscus 40.

While particular embodiments and aspects have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not be limited to the particular embodiments illustrated by the drawings and described in the specification, but that the present teachings will include any embodiments falling within the foregoing description and the appended claims.

What is claimed is:

1. A fixation assembly for securing tissue to a bone or repairing tissue comprising:
   a fixation device including:
   an anchor having a hollow body and a plurality of inner longitudinal ribs defining a longitudinal passage of cruciate shape, the body comprising a cylindrical portion having external threads and a tapered tip portion, the cylindrical portion comprising a plurality of thin-walled window covers, each window cover occupying only a portion of the hollow body between adjacent threads and between adjacent ribs, such that after implantation the window covers are resorbed first relative to other portions of the cylindrical portion for defining a plurality of apertures in the cylindrical portion; and
   a plug configured to be received in the passage, the plug having an outer shape complementary to and mating with the cruciate shape of the passage; and
   an inserter assembly including:
   an anchor sleeve configured for engaging a proximal end of the anchor, wherein the anchor sleeve is sized to receive the plug for insertion into the longitudinal passage of the anchor; and
   a driver configured for engaging the longitudinal passage of the anchor through the anchor sleeve.

2. The fixation assembly of claim 1, wherein the tapered tip portion comprises a partial winding that extends less than one complete turn around the tapered tip portion.

3. The fixation assembly of claim 2, wherein the threads of the cylindrical portion and partial winding of the tapered tip portion have blunt non-cutting edges.

4. The fixation assembly of claim 1, wherein the longitudinal ribs include curved lobes.

5. The fixation assembly of claim 4, wherein the longitudinal ribs comprise asymmetric curved lobes defining an asymmetric passage.

6. The fixation assembly of claim 5, wherein the lobes are configured to engage a driver having a symmetric cruciate shape.

7. The fixation assembly of claim 1, wherein the plug comprises osteoinductive/osteoconductive material.

8. The fixation assembly of claim 7, wherein the plug is made of material selected from the group consisting of calcium phosphate, calcium sulfate, tricalcium phosphate, allograft bone, autograft bone, demineralized bone matrix, coral material, ProOsteon, and combinations thereof.

9. The fixation assembly of claim 1, wherein the driver is cannulated.

10. A fixation assembly for securing tissue to a bone or repairing tissue, the fixation assembly comprising:
    a fixation device including:
    an anchor having an anchor body, the anchor body including:
    a plurality of longitudinal ribs positioned to define a hollow interior passage;
    a thread extending about the plurality of longitudinal ribs; and
    a plurality of thin-walled portions extending between the plurality of longitudinal ribs and the thread, the plurality of thin-walled portions preferentially resorbable relative to the longitudinal ribs and the thread, such that, upon implantation, the thin-walled portions are first resorbed and gradually define a plurality of apertures through the anchor body; and
    a plug configured to be received in at least a portion of the interior passage, wherein the portion of the interior passage that receives the plug and the plug have mating cruciate shapes; and
    an inserter assembly including:
    an anchor sleeve having a distal end configured for engaging a proximal end of the anchor, the anchor sleeve defining a sleeve passage;
    a tubular element coupled to the proximal end of the sleeve passage, the tubular element shaped to matingly receive the plug for insertion into the interior passage of the anchor; and
    a plug sleeve having a cruciate shape, the plug sleeve removably engageable with the tubular member and shaped to matingly receive the plug for insertion into the interior passage of the anchor; and
    a driver configured for engaging the interior passage of the anchor through the plug sleeve, the tubular element and the sleeve passage.

11. The fixation assembly of claim 10, wherein the longitudinal ribs are substantially parallel.

12. The fixation assembly of claim 10, wherein the anchor further comprises a tapered tip portion having a partial winding that extends less than one complete turn around the tapered tip portion.

13. The fixation assembly of claim 10, wherein the driver is cannulated.

* * * * *